(12) United States Patent  
Ishii

(10) Patent No.: US 9,025,726 B2
(45) Date of Patent: May 5, 2015

(54) RADIATION IMAGING APPARATUS AND IMAGE PROCESSING METHOD

(71) Applicant: FUJIFILM Corporation, Tokyo (JP)

(72) Inventor: Hiroyasu Ishii, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

(21) Appl. No.: 13/629,293

(22) Filed: Sep. 27, 2012

(65) Prior Publication Data

US 2013/0083893 A1 Apr. 4, 2013

(30) Foreign Application Priority Data

Oct. 4, 2011 (JP) ................................. 2011-219888

(51) Int. Cl.
*A61B 6/00* (2006.01)
*G01N 23/20* (2006.01)

(52) U.S. Cl.
CPC .......... *A61B 6/484* (2013.01); *G01N 23/20075* (2013.01); *G21K 2207/005* (2013.01); *G01N 2223/304* (2013.01); *G01N 2223/401* (2013.01); *A61B 6/4291* (2013.01)

(58) Field of Classification Search
CPC ................................................ G21K 2207/005
USPC ............. 378/2, 4, 16, 36, 62, 70, 71, 85, 145; 382/132
See application file for complete search history.

(56) References Cited

U.S. PATENT DOCUMENTS

| | | | |
|---|---|---|---|
| 7,180,979 B2 | 2/2007 | Momose | |
| 2010/0290590 A1* | 11/2010 | Ouchi et al. | 378/62 |
| 2011/0158493 A1* | 6/2011 | Nagai et al. | 382/128 |

FOREIGN PATENT DOCUMENTS

| | | | |
|---|---|---|---|
| JP | 2011-045655 A | 3/2011 | |
| WO | WO2004/058070 A1 | 7/2004 | |
| WO | WO2011149033 | * 12/2011 | ............... A61B 6/00 |

OTHER PUBLICATIONS

Meneses et al., Phase-unwrapping algorithm for images with high noise content based on a local histogram, Mar. 2005, Applied Optics, vol. 44, No. 7, pp. 1207-1214.*
Extended European Search Report dated Jan. 24, 2013.

* cited by examiner

*Primary Examiner* — Glen Kao
*Assistant Examiner* — Julio M Duarte-Carvajalin
(74) *Attorney, Agent, or Firm* — McGinn IP Law Group, PLLC

(57) ABSTRACT

A radiation imaging apparatus includes a differential phase image producing section, a phase unwrapping section, a statistical operation section, and a correction processing section. The differential phase image producing section produces a differential phase image in which pixel values are wrapped into a predetermined range α. The phase unwrapping section performs a phase unwrapping process to the differential phase image. The statistical operation section obtains a mode from statistical operation of pixel values in each subregion segmented in the unwrapped differential phase image. Each subregion is a unit in which error caused by the phase unwrapping process is to be corrected. The correction processing section calculates, for each pixel, an integer "n" which allows a difference Δ between the mode and a pixel value of each pixel to satisfy $n\alpha - \alpha/2 \le \Delta < n\alpha + \alpha/2$, and subtracts $n \cdot \alpha$ from each pixel value.

20 Claims, 13 Drawing Sheets

US 9,025,726 B2

RADIATION IMAGING APPARATUS AND IMAGE PROCESSING METHOD

BACKGROUND OF THE INVENTION

1. Field of the Invention

The present invention relates to a radiation imaging apparatus for detecting an image based on a phase shift of radiation caused by a subject and an image processing method for use in a radiation imaging apparatus.

2. Description Related to the Prior Art

Radiation, for example, X-rays are attenuated depending on weight (atomic number) of an element constituting the substance, and density and thickness of the substance. By taking advantage of the characteristics of this attenuation, the X-rays are used as a probe for examining the inside of a subject in medical diagnoses and non-destructive inspections.

A common X-ray imaging apparatus is provided with an X-ray source for emitting the X-rays and an X-ray image detector for detecting the X-rays. A subject is placed between the X-ray source and the X-ray image detector. The X-rays emitted from the X-ray source are attenuated or absorbed by the subject and then are incident on the X-ray image detector. As a result, the image reflecting the intensity changes of the X-rays caused by the subject is detected using the X-ray image detector.

The X-ray absorption performance of a substance decreases as the atomic number of the element constituting the substance decreases. This causes a problem that a sufficient contrast cannot be obtained in the X-ray absorption image of living soft tissue or soft materials. For example, a cartilage portion constituting a joint of a human body and synovial fluid surrounding the cartilage portion are mainly composed of water, so that there is little difference between their amounts of X-ray absorption, resulting in little difference in contrast.

Recently, X-ray phase imaging has been studied actively to solve the above problem. The X-ray phase imaging is used to obtain an image (hereafter referred to as the phase contrast image) based on a phase shift, instead of an intensity change, of the X-rays caused by the subject through which the X-ray passes. The X-ray phase imaging is a method to image the phase shift of the X-rays based on the fact that the phase shift of the X-rays is larger in magnitude than the intensity change of the X-rays when the X-rays are incident on the subject. Thereby, a high contrast image is obtained even if the subject is composed of components with little difference in X-ray absorptivity. An X-ray imaging apparatus using an X-ray Talbot interferometer to detect the phase shift of the X-rays is known as one type of X-ray phase imaging apparatus. The X-ray Talbot interferometer uses two diffraction gratings and an X-ray image detector (see, for example, U.S. Pat. No. 7,180,979 (corresponding to WO2004/058070).

In the X-ray imaging apparatus, when viewed from the X-ray source, a first diffraction grating is disposed behind the subject. A second diffraction grating is placed downstream of the first diffraction grating by a Talbot length. The X-ray image detector is disposed behind the second diffraction grating. The Talbot length is a distance between the first diffraction grating and a position at which the X-rays passed through the first diffraction grating form a self image (fringe image) of the first diffraction grating due to the Talbot effect. The Talbot length is determined by a grating pitch of the first diffraction grating and an X-ray wavelength. The self image is modulated by refraction of the X-rays due to the phase shift caused by the subject. An image representing the phase shift is produced by detecting an amount of modulation.

A fringe scanning method is known as a method to detect the amount of modulation. In the fringe scanning method, the second diffraction grating is translationally moved (scanned), relative to the first diffraction grating, at a predetermined scanning pitch in a direction parallel to the first diffraction grating and vertical to a grating line (grid line) of the first diffraction grating. Every time the second diffraction grating is moved, the X-ray source emits the X-rays and the X-ray detector images the X-rays passed through the subject and the first and second diffraction gratings. A phase shift value (a phase difference from an initial position in the absence of the subject) is calculated from an intensity modulation signal that represents changes in pixel value of each pixel obtained with the X-ray image detector during the scanning. Thereby, an image related to the amount of modulation is produced. The image, referred to as the differential phase image, reflects a refraction index of the subject, and corresponds to a differential value of the phase shift of the X-rays.

As disclosed in the U.S. Patent No. 7,180,979, the phase shift value is calculated using a function (arg[ . . . ]) to extract an argument of a complex number or an arctangent function ($\tan^{-1}$[ . . . ]). Accordingly, the differential phase image is represented by values wrapped into a range (of $-\pi$ to $\pi$, or of $-\pi/2$ to $+\pi/2$) of the function. The "wrapped" differential phase image may have a phase discontinuity at a data point where the value changes from the upper limit to the lower limit or from the lower limit to the upper limit of the range. A phase unwrapping process is carried out to eliminate the phase discontinuity and make values change smoothly (for example, see Japanese Patent Laid-Open Publication No. 2011-045655).

The phase unwrapping process starts from a starting point in the differential phase image and is carried out sequentially along a path. When the phase discontinuity is detected in the path, a value corresponding to the range of the above-described function is added to or subtracted from each data on and after to the phase discontinuity. Thereby, the phase discontinuity is eliminated, making the data continuous.

When the subject includes a body part having high X-ray absorption characteristics, for example, a bony part, the body part significantly attenuates the X-rays. This reduces intensity and amplitude of the intensity modulation signal. The calculation accuracy of the phase shift value is reduced in a region with the body part having the high X-ray absorption characteristics, which often results in phase unwrapping error. The phase unwrapping error occurs when the phase unwrapping process is performed on a normal data point mistakenly detected as the phase discontinuity. The phase unwrapping error also occurs when the phase discontinuity is mistakenly detected as the normal data point and the phase unwrapping process is not performed.

For example, when the bony part is on the path of the phase unwrapping process and causes the phase unwrapping error, an error value (corresponding to the range of the above-described function) is added to the subsequent data on the path. This causes streak noise in the differential phase image in a direction of the path of the phase unwrapping process. When the streak noise overlaps with soft tissue, for example, the cartilage portion, the streak noise hinders imaging of the soft tissue, being a region of interest in the X-ray phase imaging.

SUMMARY OF THE INVENTION

An object of the present invention is to provide a radiation imaging apparatus for correcting phase unwrapping error to obtain a differential phase image free from streak noise, and an image processing method for correcting phase unwrapping error.

A radiation imaging apparatus of the present invention includes a radiation image detector, a grating unit, a differential phase image producing section, a phase unwrapping section, a statistical operation section, and a correction processing section. The radiation image detector detects radiation, emitted from a radiation source and passed through a subject, and produces image data. The grating unit is disposed between the radiation source and the radiation image detector. The differential phase image producing section produces a differential phase image based on the image data obtained with the radiation image detector. The differential phase image has pixel values wrapped into a value $\alpha$ within a range of $-\alpha$ to $+\alpha$. The phase unwrapping section performs phase unwrapping process to the differential phase image. The statistical operation section obtains a reference value from statistical operation of pixel values of pixels in each subregion segmented in the differential phase image after the phase unwrapping process. The subregion is a unit in which error caused by the phase unwrapping process is to be corrected. The correction processing section corrects error caused by the phase unwrapping processing. The correction processing section calculates an integer n for each pixel with the pixel value different from the reference value in the subregion. The integer n allows a difference $\Delta$ between a reference value and the pixel value to satisfy $n\alpha-\alpha/2 \leq \Delta < n\alpha+\alpha/2$. The correction processing section subtracts $n\cdot\alpha$ from the each pixel value.

It is preferable that the reference value is a mode of the pixel values in the subregion.

It is preferable that the radiation imaging apparatus further includes a size determination section for determining size of the subregion based on the differential phase image after the phase unwrapping process.

It is preferable that the size determination section calculates a maximum variation between the pixel values in the differential phase image based on an average pixel value in each of predetermined regions in the differential phase image. It is preferable that the size determination section determines the size of the subregion based on a ratio between the maximum variation and size of the differential phase image.

It is preferable that the regions are positioned in four respective corners of the differential phase image.

It is preferable that the size determination section determines the size of the subregion in accordance with a ratio of the size of the differential phase image such that a variation between the pixel values in the subregion is less than or equal to a value $\alpha$ within a range of $-\alpha$ to $\alpha$.

It is preferable that the size determination section calculates the maximum variation between the pixel values in each of a width direction, a length direction, and a diagonal direction of the differential phase image based on the average pixel value. It is preferable that the size determination section determines a width of the subregion based on the maximum variation in the width direction and the maximum variation in the diagonal direction. It is preferable that the size determination section determines a length of the subregion based on the maximum variation in the length direction and the maximum variation in the diagonal direction.

It is preferable that the subregions are positioned to segment the whole differential phase image.

It is preferable that the adjacent subregions are positioned to overlap each other.

It is preferable that the radiation imaging apparatus further includes a storage section and an offset processing section. The storage section stores the differential phase image, captured in absence of the subject, as an offset image. The offset processing section subtracts the offset image from the differential phase image with the phase unwrapping error corrected.

It is preferable that the grating unit is composed of a first grating and a second grating. The first grating passes the radiation from the radiation source to form a first periodic pattern image, and the second grating partly blocks the first periodic pattern image to form a second periodic pattern image, and the radiation image detector detects the second periodic pattern image to produce the image data.

It is preferable that the grating unit is provided with a scan mechanism. The scan mechanism moves the first grating or the second grating at a predetermined scan pitch and puts the first grating or the second grating to each of scan positions sequentially. The radiation image detector detects the second periodic pattern image and produces the image data every time the first grating or the second grating is moved to one of the scan positions. The differential phase image producing section produces the differential phase image based on the image data produced by the radiation image detector.

It is preferable that the scan mechanism moves the first grating or the second grating in a direction orthogonal to a grating line.

It is preferable that the scan mechanism moves the first grating or the second grating in a direction tilted relative to a grating line.

It is preferable that the differential phase image producing section produces the differential phase image based on the single image data obtained with the radiation image detector.

It is preferable that the first grating is an absorption grating that projects the incident radiation in a geometrical-optical manner to produce the first periodic pattern image.

It is preferable that the first grating is an absorption grating or a phase grating, and the first grating produces Talbot effect to produce the first periodic pattern image.

It is preferable that the radiation imaging apparatus further includes a multi-slit for partly blocking the radiation from the radiation source to disperse a focal spot.

An image processing method of the present invention includes an unwrapping step, a segmenting step, a statistical operation step, a calculating step, a correcting step, and a repeating step. In the unwrapping step, a phase unwrapping process is performed to a differential phase image having pixel values wrapped into a range $\alpha$. In the segmenting step, the differential phase image is segmented into subregions after the unwrapping step. Each of the subregions is a unit in which phase unwrapping error is to be corrected. Each of the subregions contains pixels. In the statistical operation step, a reference value is obtained from statistical operation of the pixel values of the pixels in the subregion. In the calculating step, an integer n is calculated for each pixel with the pixel value different from the reference value in the subregion. The integer n allows a difference $\Delta$ between the reference value and each pixel value to satisfy $n\alpha-\alpha/2 \leq \Delta < n\alpha+\alpha/2$. In the correcting step, $n\cdot\alpha$ is subtracted from each pixel value different from the reference value in the subregion to correct the phase unwrapping error. In the repeating step, the statistical operation step, the calculating step, and the correcting steps are repeated until the phase unwrapping error is corrected in every subregion.

It is preferable that the image processing method includes a determining step to determine the size of each subregion based on the differential phase image after the unwrapping step and before the segmenting step.

According to the present invention, the differential phase image free from the streak noise, caused by the phase unwrapping error, is obtained.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
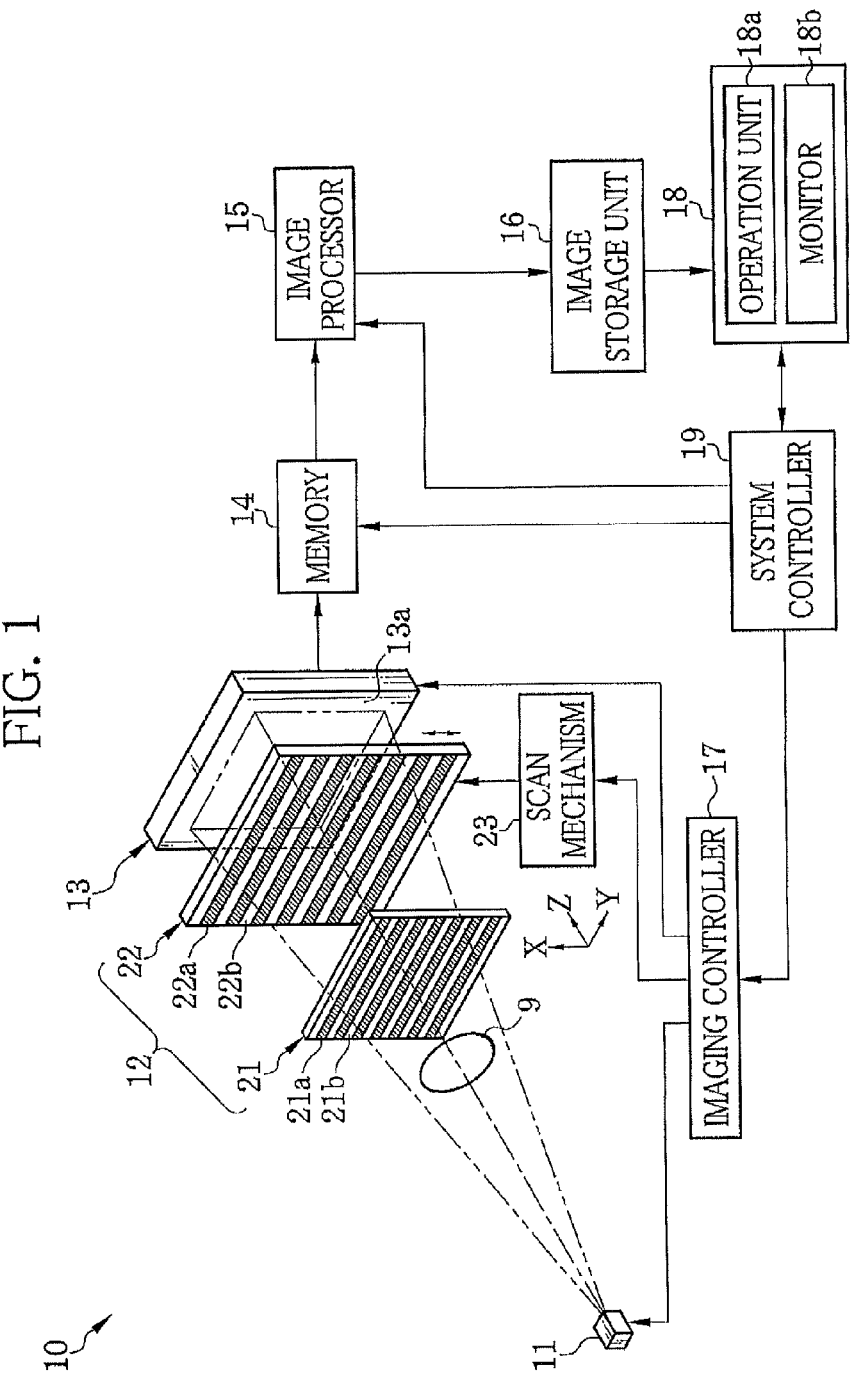
FIG. 1 is a block diagram of an X-ray imaging apparatus.

In FIG. 1, an X-ray imaging apparatus 10 is provided with an X-ray source 11, a grating unit 12, an X-ray image detector 13, a memory 14, an image processor 15, an image storage unit 16, an imaging controller 17, a console 18, and a system controller 19. The X-ray source 11 has a rotating anode type X-ray tube and a collimator, for example. The collimator limits an X-ray field. The imaging controller 17 controls the X-ray source 11 to emit X-rays toward a subject 9.

The grating unit 12 is provided with a first grating 21, a second grating 22, and a scan mechanism 23. The first and second gratings 21 and 22 are positioned opposite the X-ray source 11 in Z direction, being a direction of X-ray emission. There is a space enough to place the subject 9 between the X-ray source 11 and the first grating 21. The X-ray image detector 13 is, for example, a flat panel detector using a semiconductor circuit. The X-ray image detector 13 is disposed behind the second grating 22 such that a detection face 13a of the X-ray image detector 13 is orthogonal to the Z direction.

The first grating 21 is an absorption grating. The first grating 21 is provided with a plurality of X-ray absorbing portions 21a and a plurality of X-ray transmitting portions 21b both extending in Y direction orthogonal to the Z direction. The X-ray absorbing portions 21a and the X-ray transmitting portions 21b are arranged alternately in X direction orthogonal to the Z and Y directions, forming a stripe-like pattern. Similar to the first grating 21, the second grating 22 is an absorption grating and provided with a plurality of X-ray absorbing portions 22a and a plurality of X-ray transmitting portions 22b both extending in the Y direction and arranged alternately in the X direction. The X-ray absorbing portions 21a and 22a are formed of metal which absorbs the X-rays, for example, gold (Au), platinum (Pt), or the like. The X-ray transmitting portions 21b and 22b are gaps, or formed of an X-ray transmissive material such as silicon (Si) or resin.

A part of the X-rays emitted from the X-ray source 11 passes through the first grating 21 to form a first periodic pattern image (hereinafter referred to as the G1 image). A part of the G1 image passes through the second grating 22 to form a second periodic pattern image (hereinafter referred to as the G2 image). In other words, the second grating 22 partly blocks the G1 image to form the G2 image. In the absence of the subject 9, the G1 image substantially coincides with a grating pattern of the second grating 22.

The X-ray image detector 13 detects the G2 image to produce image data. The memory 14 temporarily stores the image data read out from the X-ray image detector 13. The image processor 15 produces a differential phase image based on the image data stored in the memory 14, and produces a phase contrast image based on the differential phase image. The image storage unit 16 stores the differential phase image and the phase contrast image.

The scan mechanism 23 translationally moves the second grating 22 in the X direction so as to successively change a position of the second grating 22 relative to the first grating 21. The scan mechanism is composed of a piezoelectric actuator or an electrostatic actuator. The imaging controller 17 controls and drives the scan mechanism 23 to carry out fringe scanning, which will be described below. Image data obtained at respective scan positions of the fringe scanning using the X-ray image detector 13 is stored in the memory 14.

The console 18 is provided with an operation unit 18a and a monitor 18b. The operation unit 18a is composed of a mouse, a keyboard, and the like. The operation unit 18a is used to set imaging conditions such as a tube voltage, a tube current, and exposure time, to switch between imaging modes, and to input an operation command to carry out the imaging, for example. The imaging modes include a preliminary imaging mode and a main imaging mode. In the main imaging mode, the imaging (hereinafter may referred to as the main imaging) is performed with the subject 9 placed between the X-ray source 11 and the first grating 21. In the preliminary imaging mode, the imaging (hereinafter may referred to as the preliminary imaging) is performed in the absence of the subject 9. The preliminary imaging is performed to obtain a background component, caused by manufacturing error or alignment error of the first and second gratings 21 and 22, as an offset image, which will be described below.

The monitor 18b displays the differential phase image and the phase contrast image, both stored in the image storage unit 16, and imaging information such as the imaging conditions. The system controller 19 controls each section in response to a signal inputted from the operation unit 18a.

Figure 2:
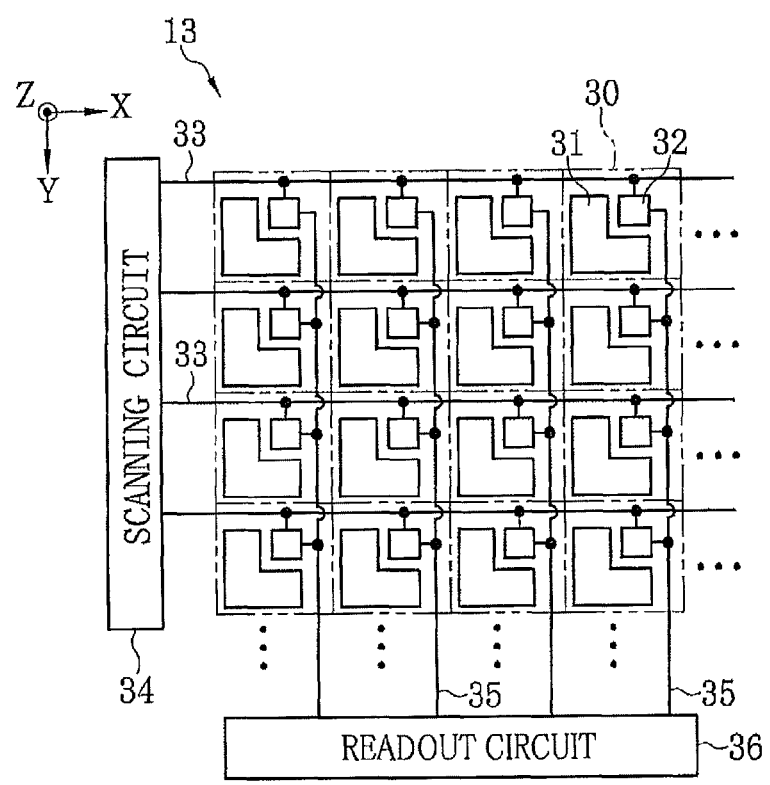
FIG. 2 is a schematic view of an X-ray image detector.

In FIG. 2, the X-ray image detector 13 has a plurality of pixel units 30 arranged in two-dimensions. Each pixel unit 30 is provided with a pixel electrode 31 and a TFT (Thin Film Transistor) 32. The pixel electrode 31 collects charge generated in a semiconductor film (not shown) due to the incident X-rays. The TFT 32 is used to read out the charge collected by the pixel electrode 31. The semiconductor film is formed from amorphous selenium, for example.

The X-ray image detector 13 is provided with gate scanning lines 33, a scanning circuit 34, signal lines 35, and a readout circuit 36. The gate scanning line 33 is provided per row of the pixel units 30. The scanning circuit 34 supplies each gate scanning line 33 with a scan signal to turn on and off the TFT 32. The signal line 35 is provided per column of the pixel units 30. The readout circuit 36 reads the charge from the pixel units 30 through the signal line 35, and converts the charge into image data and outputs the image data. A layer configuration of the pixel unit 30 is similar to that disclosed in Japanese Patent Laid-Open Publication No. 2002-26300, for example.

The readout circuit 36 is provided with an integrating amplifier, an A/D converter, a correction circuit, and the like (all not shown). The integrating amplifier integrates the charge outputted from each pixel unit 30 through the signal line 35 to generate an image signal. The A/D converter converts the image signal, generated by the integrating amplifier, into digital image data. The correction circuit performs, for example, dark current correction, gain correction, and linearity correction to the image data. Thereafter, the image data is stored in the memory 14.

The X-ray image detector 13 is not limited to a direct conversion type that uses the semiconductor film to directly convert the incident X-rays into the charge. The X-ray image detector 13 may be an indirect conversion type that uses a scintillator made from cesium iodide (CsI), gadolinium oxysulfide (GOS), or the like to convert the incident X-rays into visible light and a photodiode to convert the visible light into the charge. The X-ray image detector 13 may be provided with a combination of the scintillator and a CMOS sensor.

Figure 3:
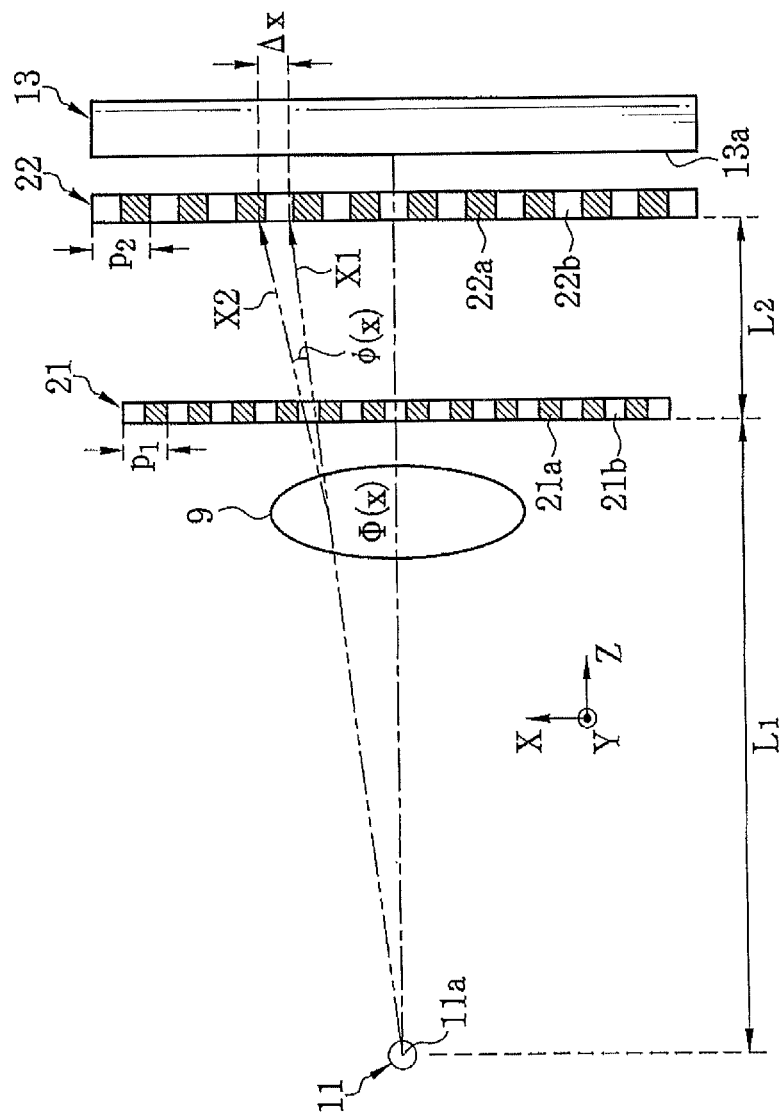
FIG. 3 is an explanatory view of first and second gratings.

In FIG. 3, the X-ray source 11 emits the cone-shaped X-ray beams from an X-ray focal spot 11a, being a light emission point. The first grating 21 is configured to project the X-rays, passed through the X-ray transmitting portions 21b, in a substantially geometrical-optical manner without causing Talbot effect. To be more specific, a width of the X-ray transmitting portion 21b in the X direction is sufficiently larger than a peak wavelength of the X-rays emitted from the X-ray source 11. Thereby, most of the X-rays do not diffract through the first grating 21. For example, when the rotating anode of the X-ray source 11 is made from tungsten and the tube voltage is set to 50 kV, the peak wavelength of the X-rays is approximately 0.4 Å. In this case, the width of the X-ray transmitting portion 21b is of the order of 1 to 10 µm.

Thereby, the G1 image, being a self image of the first grating 21, is formed at any position downstream from the first grating 21 in the Z direction regardless of a distance from the first grating 21.

As described above, a grating pitch $p_2$ of the second grating 22 is set such that the grating pattern of the second grating 22 coincides with the G1 image formed at the position of the second grating 22. To be more specific, the grating pitch $p_2$ of the second grating 22 is set to substantially satisfy an expression (1), where $p_1$ denotes a grating pitch of the first grating 21, $L_1$ denotes a distance between the X-ray focal spot 11a and the first grating 21, and $L_2$ denotes a distance between the first grating 21 and the second grating 22.

$$p_2 = \frac{L_1 + L_2}{L_1} p_1 \tag{1}$$

The G1 image is modulated by the phase shift of the X-rays caused by the X-ray refraction when the X-rays are incident on the subject 9. An amount of the modulation reflects an angle of refraction $\phi(x)$ of the X-rays refracted by the subject 9. FIG. 3 shows a path of the X-rays refracted in accordance with a phase shift distribution $\Phi(x)$ representing the phase shift of the X-rays caused by the subject 9. In the absence of the subject 9, the X-rays travel linearly in a path "X1". In this example, the X-rays in the path X1 pass through the first and second gratings 21 and 22 and then are incident on the X-ray image detector 13. When the subject 9 is placed between the X-ray source 11 and the first grating 21, the X-rays refracted by the subject 9 travel in a path "X2". The X-rays in the path "X2" pass through the first grating 21, but are incident on and absorbed by the X-ray absorbing portion 22a of the second grating 22.

The phase shift distribution $\Phi(x)$ is represented by an expression (2), where λ denotes the wavelength of the X-rays and n(x, z) denotes a refractive index distribution of the subject 9.

$$\Phi(x) = \frac{2\pi}{\lambda} \int [1 - n(x, z)] dz \tag{2}$$

The refraction angle $\phi(x)$ relates to the phase shift distribution $\Phi(x)$ such that they satisfy an expression (3):

$$\phi(x) = \frac{\lambda}{2\pi} \frac{\partial \Phi(x)}{\partial x} \tag{3}$$

At the position of the second grating 22, the X-rays are displaced in the X direction by an amount corresponding to the refraction angle $\phi(x)$. A displacement amount $\Delta x$ is represented substantially by an expression (4) because the refraction angle $\phi(x)$ of the X-rays is minute.

$$\Delta x \approx L_2 \phi(x) \tag{4}$$

As described above, the displacement amount $\Delta x$ is in proportion to a differential value of the phase shift distribution $\Phi(x)$. Accordingly, the differential value of the phase shift distribution $\Phi(x)$ is obtained by detecting the displacement amount $\Delta x$ using the fringe scanning. Thus, the differential phase image is produced.

The fringe scanning is performed as follows. The scan mechanism 23 translationally moves the second grating 22 at the scanning pitch that is the grating pitch $p_2$ divided by a number M ($p_2/M$). Every time the second grating 22 is moved translationally, the X-ray source 11 emits the X-rays and the X-ray image detector 13 captures the G2 image. The number M is an integer greater than or equal to 3. It is preferable that M=5, for example.

Moiré fringes occur in the G2 image when the gratings are set to be slightly different from the expression (1) or when the first grating 21 and/or the second grating 22 is rotated relative to the Z direction or slightly tilted relative to the XY plane. The moiré fringes moves with the translational movement of the second grating 22. When the distance of the movement in the X direction reaches the length of the grating pitch $p_2$, the moiré fringes return to the original positions. The amount of the translational movement of the second grating 22 is obtained from the movements of the moiré fringes.

Figure 4:
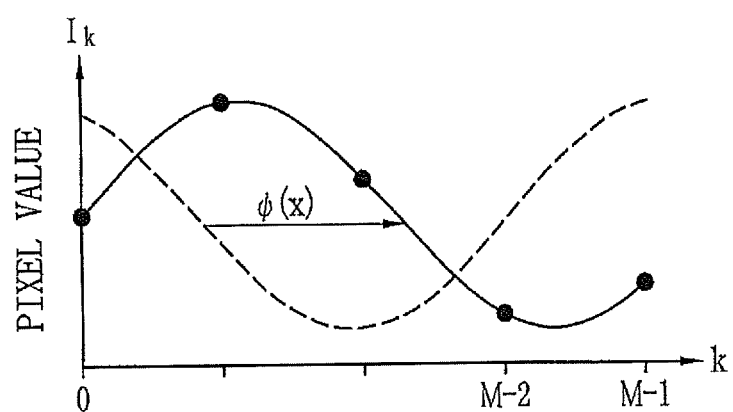
FIG. 4 is a graph showing an intensity modulation signal.

In the fringe scanning, "M" number of pixel values are obtained from each pixel unit 30 of the X-ray image detector 13. As shown in FIG. 4, the "M" number of pixel values $I_k$ vary periodically relative to respective scan positions k of the second grating 22. The scan position k refers to the position of the second grating when the second grating 22 is translationally moved by one period, namely, when the second grating 22 is moved by the scanning pitch ($p_2$/M). A signal that represents changes in the pixel values $I_k$ relative to the respective scan positions k is referred to as the intensity modulation signal.

A broken line in FIG. 4 denotes an intensity modulation signal obtained in the absence of the subject 9. A solid line denotes the intensity modulation signal obtained in the presence of the subject 9. In this case, the intensity modulation signal is shifted by a phase shift value ψ(x) caused by the subject 9.

The phase shift value ψ(x) and the displacement amount Δx satisfy an expression (5):

$$\psi(x) = \frac{2\pi}{p_2} \Delta x \quad (5)$$

Accordingly, the phase shift value Φ(x) of the intensity modulation signal is determined based on the "M" number of pixel values $I_k$ of each pixel unit 30 obtained using the fringe scanning. Thereby, the differential phase image is produced.

Next, a method for calculating the phase shift value ψ(x) is described. Generally, the intensity modulation signal is represented by an expression (6):

$$I_k = A_0 + \sum_{n>0} A_n \exp\left[ni\left\{\psi(x) + 2\pi \frac{k}{M}\right\}\right] \quad (6)$$

In the expression (6), $A_0$ denotes average intensity of the incident X-rays, $A_n$ denotes amplitude of the intensity modulation signal, "n" denotes a positive integer, and "i" denotes an imaginary unit. As shown in FIG. 4, when the intensity modulation signal is a sine wave, n=1.

In this embodiment, an expression (7) is satisfied because the scanning pitch ($p_2$/M) is constant.

$$\sum_{k=0}^{M-1} \exp\left(-2\pi i \frac{k}{M}\right) = 0 \quad (7)$$

When the expression (7) is applied to the expression (6), the phase shift value ψ(x) is represented by an expression (8):

$$\psi(x) = \arg\left[\sum_{k=0}^{M-1} I_k \exp\left(-2\pi i \frac{k}{M}\right)\right] \quad (8)$$

In the expression (8), arg[ . . . ] is a function to extract an argument of a complex number. The phase shift value ψ(x) can be represented by an expression (9) using an arctangent function.

$$\psi(x) = -\tan^{-1} \frac{\sum_{k=0}^{M-1} I_k \sin\left(2\pi \frac{k}{M}\right)}{\sum_{k=0}^{M-1} I_k \cos\left(2\pi \frac{k}{M}\right)} \quad (9)$$

The argument of the complex number is wrapped into a range of π to π. Accordingly, when the phase shift value ψ(x) is calculated based on the expression (8), the phase shift value ψ(x) is wrapped into the range of π to π. The arctangent function is normally in a range of π/2 to π/2. Accordingly, when the phase shift value ψ(x) is calculated based on the expression (9), the phase shift value ψ(x) is wrapped into the range of π/2 to π/2. Note that, in the expression (9), by distinguishing between positive/negative signs of the denominator and the numerator of the arctangent function, the range is set to be from π to π. Thereby, the phase shift value ψ(x) is calculated in the range of −π to +π.

In this embodiment, data having the phase shift value ψ(x) calculated for each of the pixel units 30, as the pixel value is referred to as the differential phase image. Note that the differential phase image may be defined as an image represented by data being the product of the phase shift value ψ(x) and a constant, or the sum of the phase shift value ψ(x) and a constant. Hereinafter, the pixel values of the differential phase image are wrapped into a predetermined range, for example, in the range of 0 to α (see FIG. 7).

Figure 5:
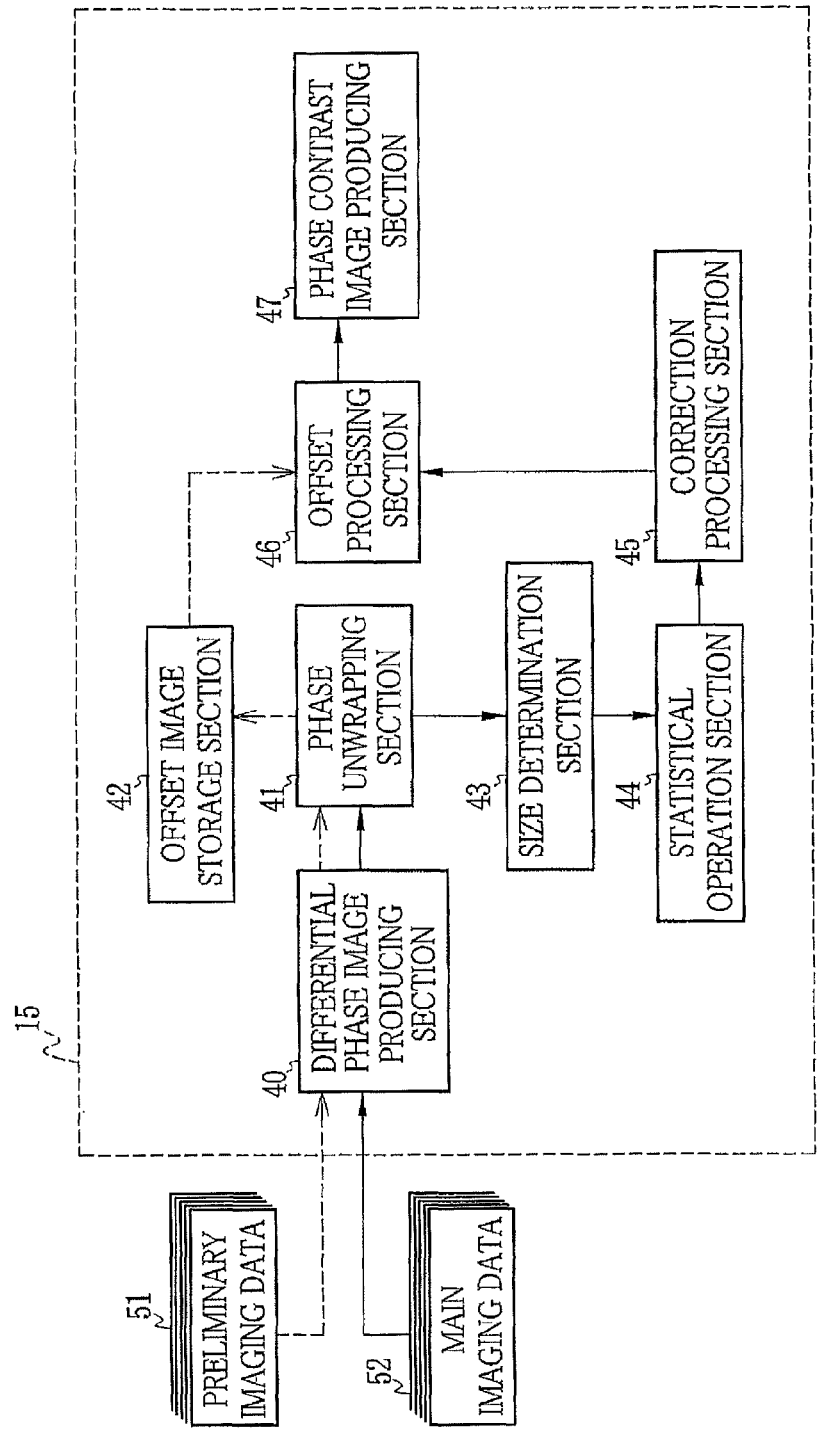
FIG. 5 is a block diagram of an image processor.

As shown in FIG. 5, the image processor 15 is provided with a differential phase image producing section 40, a phase unwrapping section 41, an offset image storage section 42, a size determination section 43, a statistical operation section 44, a correction processing section 45, an offset processing section 46, a phase contrast image producing section 47, and the like.

The differential phase image producing section 40 performs arithmetic operation based on the expression (8) or (9) with the use of M number of image data (preliminary imaging data) 51. Thereby, the differential phase image is produced. The M number of preliminary imaging data 51 is obtained with the X-ray image detector 13 using the fringe scanning in the preliminary imaging. In a similar manner, the differential phase image producing section 40 produces the differential phase image based on M number of image data (main imaging data) 52. The M number of main imaging data 52 is obtained with the X-ray image detector 13 using the fringe scanning in the main imaging.

The phase unwrapping section 41 performs a phase unwrapping process to the differential phase image inputted from the differential phase image producing section 40. In the preliminary imaging, the differential phase image producing section 40 inputs the differential phase image, produced based on the preliminary imaging data 51, to the phase unwrapping section 41. After the phase unwrapping process, the phase unwrapping section 41 stores the differential phase image, produced from the preliminary imaging data 51, as an offset image in the offset image storage section 42. Note that, when a new offset image is inputted after the subsequent preliminary imaging, the offset image storage section 42 deletes the already stored offset image and stores the new offset image.

In the main imaging, the phase unwrapping section 41 performs the phase unwrapping process to the differential phase image produced based on the main imaging data 52.

After the phase unwrapping process, the phase unwrapping section 41 inputs the differential phase image to the size determination section 43.

Figure 6:
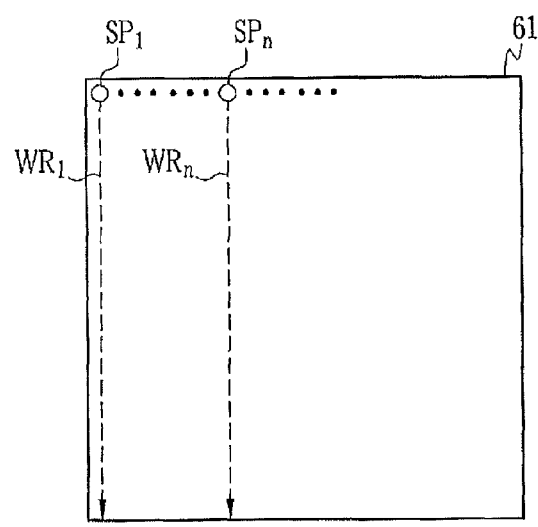
FIG. 6 is an explanatory view showing a starting point and a path of a phase unwrapping process.

As shown in FIG. 6, the phase unwrapping section 41 uses, for example, a pixel positioned in a corner of a differential phase image 61 as a starting point $SP_1$. The phase unwrapping process is carried out from the starting point $SP_1$ along a path $WR_1$. Then, the phase unwrapping process of the starting point $SP_1$ and a starting point $SP_2$ adjacent to the starting point $SP_1$ are carried out. Thereafter, the phase unwrapping process is carried out from the starting point $SP_2$ along a path $WR_2$. The processes are repeated with a new starting point $SP_n$ and a new path $WR_n$.

Figure 7:
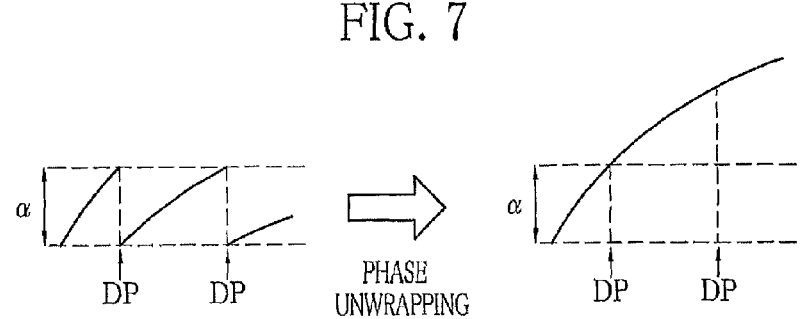
FIG. 7 is an explanatory view of the phase unwrapping process.

As shown in FIG. 7, in the phase unwrapping process, a phase discontinuity DP is detected. The phase discontinuity DP is a data point where the pixel value of the differential phase image changes significantly (referred to as the phase jump) due to the pixel values of the differential phase image wrapped in the predetermined range. The discontinuity DP is canceled by adding or subtracting a value α within the range "−α to α" to/from each of the pixel values, on and after the phase discontinuity DP, along the path WRn. Thus, the changes in the pixel values are made substantially continuous. The phase discontinuity DP is detected when the difference between the adjacent pixel values is greater than or equal to ½ of the range "α".

Figure 8:
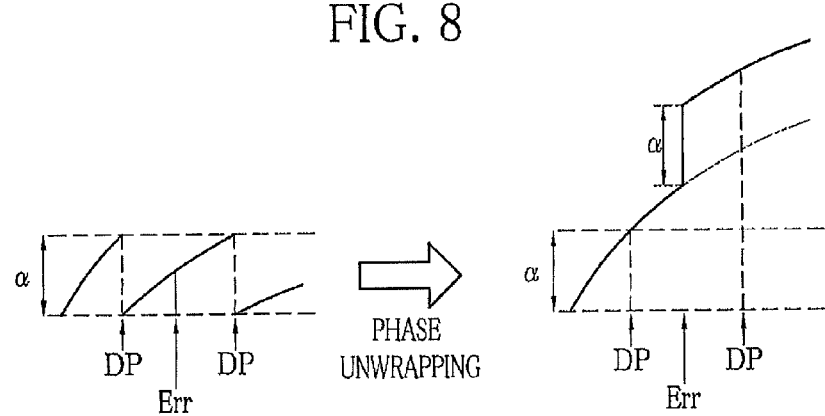
FIG. 8 is an explanatory view showing how phase unwrapping error occurs.

As shown in FIG. 8, when a phase discontinuity Err due to noise or the like exists on the path WRn, in addition to the phase discontinuity DP due to the phase jump, the phase unwrapping section 41 cannot distinguish the phase discontinuity Err from the phase discontinuity DP. In this case, the phase unwrapping section 41 mistakenly adds or subtracts a value α within the range "−α to α" to/from the phase discontinuity Err. As a result, the phase discontinuity Err causes a gap with a value α within the range "−α to α" in the differential phase image after the phase unwrapping process. The gap is referred to as the phase unwrapping error.

Note that, when the phase discontinuity Err, caused by the noise or the like, is composed of single data, the phase unwrapping process is performed with no phase unwrapping error. This is because each of the difference between the phase discontinuity Err and the preceding data point and the difference between the phase discontinuity Err and the subsequent data point exceeds the predetermined value for detecting the phase discontinuity. As a result, the phase unwrapping process is carried out to add and subtract (or to subtract and add) the range "−α to α" to/from the respective differences, which cancels out each other. On the other hand, the phase discontinuity Err shown in FIG. 8 is composed of data points. For example, the phase discontinuity Err is composed of two data points Err1 and Err2, and the difference between the data point Err1 and the preceding data point exceeds the predetermined value, but the difference between the data points Err1 and Err2 and the difference between the data point Err2 and the subsequent data point do not exceed the predetermined value. In this case, the phase unwrapping process is carried out by detecting the difference between the data point Err1 and the preceding data point. However, the difference between the data points Err1 and Err2 and the difference between the data point Err2 and the subsequent data point are not detected as the data points where the phase unwrapping process is necessary. Thus, the phase unwrapping process carried out by detecting the difference between the data point Err1 and the preceding data point results in the phase unwrapping error.

As described above, the preliminary imaging is carried out in the absence of the subject 9. Basically, the phase discontinuity Err does not occur in the preliminary imaging data 51 and the differential phase image produced from the preliminary imaging data 51, except for the phase discontinuity DP caused by the phase jump. Accordingly, the phase unwrapping error does not occur when the differential phase image produced in the preliminary imaging is subjected to the phase unwrapping process.

Figure 9:
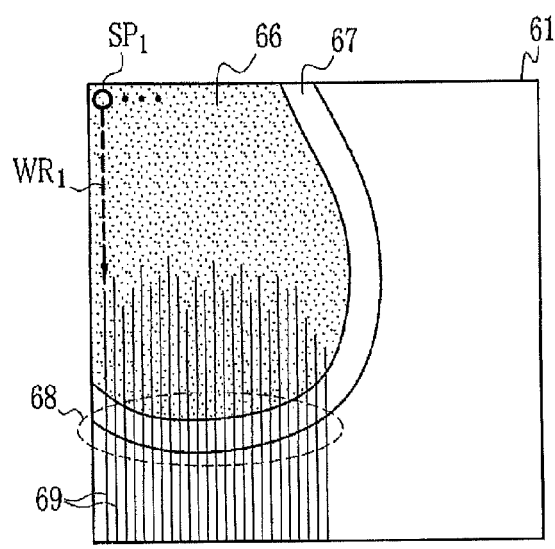
FIG. 9 is a schematic view of a differential phase image after the phase unwrapping process.

In the main imaging, the differential phase image is produced based on the main imaging data 51 obtained in the presence of the subject 9. The phase unwrapping process of the differential phase image may cause the phase unwrapping error depending on the subject 9. For example, as shown in FIG. 9, the subject 9 includes a bony part 66 and soft tissue 67 (cartilage, synovial fluid, and the like). The soft tissue 67 is the region of interest in imaging with the X-ray imaging apparatus 10. The bony part 66 has low contrast and is likely to cause noise because of its high X-ray absorption characteristics. In the differential phase image produced form the main imaging data 52, the streak noise 69 resulting from the phase unwrapping error may occur along a path $WR_n$ crossing the bony part 66. For example, in a region 68 surrounded by a broken line, the noise 69 is superposed onto the soft tissue 67. This hinders observation of the soft tissue 67, being the region of interest.

The size determination section 43, the statistical operation section 44, and the correction processing section 45 carry out the correction of the phase unwrapping error (hereinafter may be referred to as the unwrapping error correction).

Figure 10:
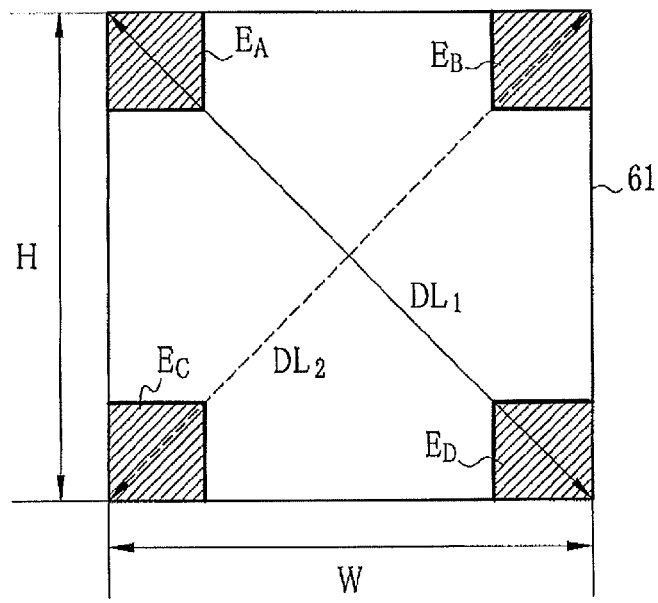
FIG. 10 is an explanatory view showing how subregions are determined by way of example.

The size determination section 43 determines the size of a unit (hereinafter referred to as the subregion), in the differential phase image 61, to be subjected to the statistical operation in the statistical operation section 44 and the correction processing in the correction processing section 45. To be more specific, as shown in FIG. 10, when the unwrapped differential phase image is inputted from the phase unwrapping section 41, the size determination section 43 extracts pixel values of respective predetermined regions $E_A$, $E_B$, $E_C$, and $E_D$.

The dimensions and the position of each of the regions $E_A$, $E_B$, $E_C$, and $E_D$ are previously determined. For example, each of the $E_A$, $E_B$, $E_C$, and $E_D$ has the width that is 10% of the width "W" of the differential phase image 61 and the length (height) that is 10% of the length "H" of the differential phase image 61 (namely, 0.1W×0.1H). To precisely determine the size of the subregion, the regions $E_A$, $E_B$, $E_C$, and $E_D$ are disposed in positions as distant from each other as possible. For example, the region $E_A$ is disposed in an upper left corner of the differential phase image 61. The region $E_B$ is disposed in an upper right corner of the differential phase image 61. The region $E_C$ is disposed in a lower left corner of the differential phase image 61. The region $E_D$ is disposed in a lower right corner of the differential phase image 61.

The size determination section 43 calculates average pixel values $\mu_A$, $\mu_B$, $\mu_C$, and $\mu_D$ of the extracted pixel values for regions $E_A$, $E_B$, $E_C$, and $E_D$, respectively. Based on the average pixel values $\mu_A$, $\mu_B$, $\mu_C$, and $\mu_D$, the size determination section 43 calculates maximum variations, between the average pixel values, $N_W$ in a width (W) direction, $N_H$ in a length (H) direction, $N_{DL1}$ in $DL_1$ direction, and $N_{DL2}$ in $DL_2$ direction. The $DL_1$ and $DL_2$ directions are diagonal directions. The variations between the average pixel values are due to offset or the like superposed on the differential phase image 61.

To calculate the maximum variation $N_W$, $N_{AB}=|\mu_A-\mu_B|$ representing a variation between the average pixel value $\mu_A$ of the region $E_A$ and the average pixel value $\mu_B$ of the region $E_B$ is calculated, and $N_{CD}=|\mu_C-\mu_D|$ representing a variation between the average pixel value $\mu_C$ of the region $E_C$ and the average pixel value $\mu_D$ of region $E_D$ is calculated. The greater of the $N_{AB}$ and $N_{CD}$ is used as the maximum variation $N_W$ in the W direction.

In a similar manner, to calculate the maximum variation $N_H$ in the H direction, $N_{AC}=|\mu_A-\mu_C|$ representing the variation between the average pixel value $\mu_A$ of the region $E_A$ and the average pixel value $\mu_C$ of the region $E_C$ is calculated, and $N_{BD}=|\mu_B-\mu_D|$ representing the variation between the average pixel value $\mu_B$ of the region $E_B$ and the average pixel value $\mu_D$ of the region $E_D$ is calculated. The greater of the $N_{AC}$ and $N_{BD}$ is used as the maximum variation $N_H$ in the H direction. The maximum variations $N_{DL1}$ and $N_{DL2}$ in the diagonal ($DL_1$ and $DL_2$) directions are calculated using $|\mu_A-\mu_D|$ and $|\mu_B-\mu_C|$, respectively.

Based on the maximum variations $N_W$, $N_H$, $N_{DL1}$, and $N_{DL2}$, the size determination section 43 determines the size of the subregion such that the variation between the pixel values in the subregion does not exceed "$\alpha$" being the range of the differential phase image before the phase unwrapping process. To be more specific, to determine the width of the subregion, the size determination section 43 determines a first reference width, a second reference width, and a third reference width based on the maximum variations $N_W$, $N_{DL1}$, and $N_{DL2}$.

The first reference width is $\alpha(W/NW)$. The variation (amount of change) between the pixel values in the width (W)direction coincides with a value $\alpha$ within the range "$-\alpha$ to $\alpha$". The second reference width is calculated by projecting $\alpha(DL1/NDL1)$, that is, the length in the diagonal direction DL1, to the side in the W direction of the differential phase image 61. When the differential phase image 61 is a square, the second reference width is $\alpha(DL1/NDL1)\times\cos 45°$. When the variation between the pixel values in diagonal direction DL1 coincides with a value $\alpha$ within the range "$-\alpha$ to $\alpha$", the second reference width corresponds to the width projected in the W direction. In a similar manner, a third reference width is calculated by projecting $\alpha(DL2/NDL2)$, that is, the length in the diagonal direction DL2, to the side in the W direction of the differential phase image 61. When the variation between the pixel values in the diagonal direction DL2 coincides with a value $\alpha$ within the range "$-\alpha$ to $\alpha$", the third reference width corresponds to the width projected in the W direction.

The size determination section 43 calculates a width which is less than or equal to the shortest of the first to the third reference widths and which divides the width W of the differential phase image 61 without a remainder. The calculated width is determined as the width of the subregion. Thereby, the variation between the pixel values in the W direction in the subregion is less than or equal to a value $\alpha$ within the range "$-\alpha$ to $\alpha$".

In a manner similar to the above, the size determination section 43 calculates a first reference length, a second reference length, and a third reference length based on the maximum variations $N_H$, $N_{DL1}$, and $N_{DL2}$, to determine the length of the subregion.

The first reference length is $\alpha(W/NH)$. The variation between the pixel values in the H direction coincides with a value $\alpha$ within the range "$-\alpha$ to $\alpha$". The second reference length is calculated by projecting the length $\alpha(DL1/NDL1)$, in the diagonal direction DL1, to the side (in the H direction) of the differential phase image. When the differential phase image is a square, the second reference length is $\alpha(DL1/NDL1)\times\sin 45°$. When the variation between the pixel values in the diagonal direction DL1 coincides with a value $\alpha$ within the range "$-\alpha$ to $\alpha$", the second reference length corresponds to the length projected in the H direction. In a similar manner, a third reference length is calculated by projecting a length $\alpha(DL2/NDL2)$, in the diagonal direction DL2, to the side (in the H direction) of the differential phase image 61. When the variation between the pixel values in the diagonal direction DL2 coincides with a value $\alpha$ within the range "$-\alpha$ to $\alpha$", the third reference length corresponds to the length projected in the H direction.

The size determination section 43 calculates the length which is less than or equal to the shortest of the first to third reference length and which divides the length H of the differential phase image 61 without a remainder. The calculated length is determined as the length of the subregion. Thereby, the variation between the pixel values in the H direction in the subregion is less than or equal to a value $\alpha$ within the range "$-\alpha$ to $\alpha$".

Figure 11:
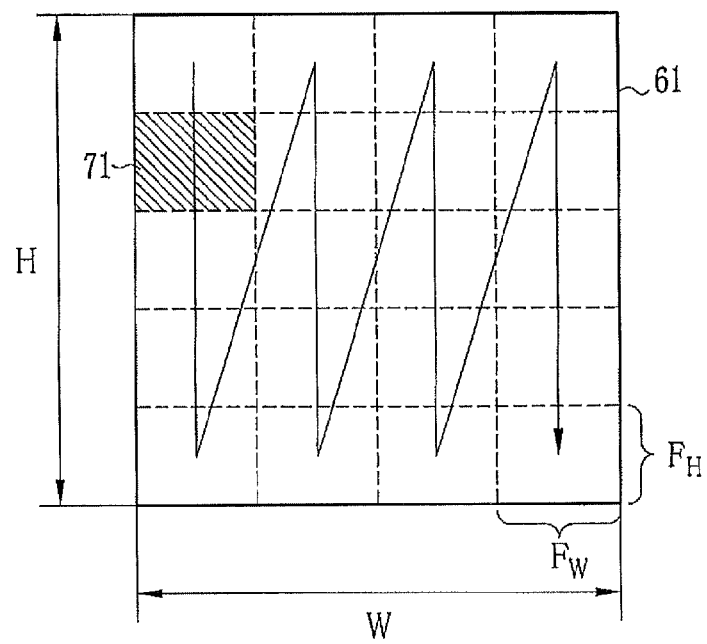
FIG. 11 is an explanatory view showing how the phase unwrapping error is corrected.

As shown in FIG. 11, the statistical operation section 44 segments the differential phase image 61 into subregions 71. Each subregion 71 has a width $F_W$ and a length $F_H$ determined by the size determination section 43. The statistical operation section 44 performs statistical operation to each of the subregions 71. The statistical operation is performed in an order indicated by an arrow, for example. Note that, in FIG. 11, the size determination section 43 determines the width $F_W$ of the subregion 71 to be W/4 and the length $F_H$ of the subregion 71 to be H/5, by way of example.

Figure 12:
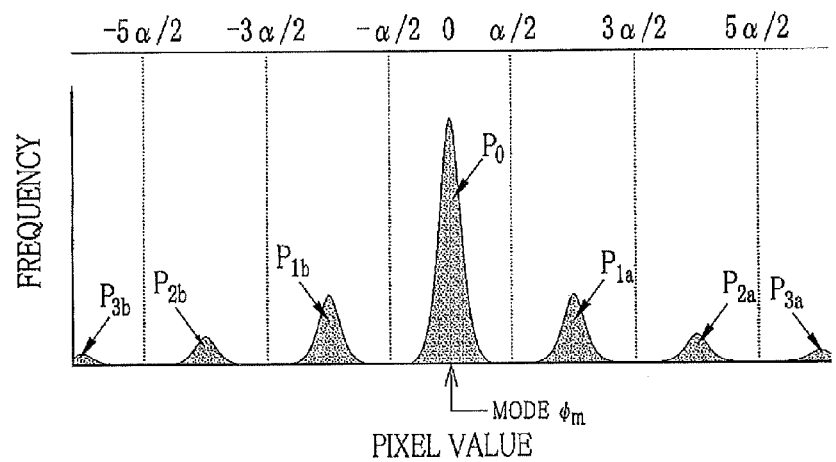
FIG. 12 is a frequency histogram showing frequency of the pixel values.

The statistical operation section 44 first examines frequency distribution of pixel values $\psi$ in the subregion 71 to obtain a mode $\psi m$. For example, as shown in FIG. 12, when the frequency distribution of the pixel values $\psi$ in the subregion 71 is made into a histogram, subdistributions such as P0, P1a, P1b, P2a, P2b, P3a and P3b appear. Each subdistribution has a value $\alpha$ within a range of approximately "$-\alpha$ to $\alpha$". The mode $\psi m$ is approximately an average value in the subdistribution P0.

Out of the subdistributions P0, P1a, P1b, P2a, P2b, P3a, and P3b, the subdistribution P0 including the mode $\psi m$ does not substantially have a gap caused by the phase unwrapping error and contains normal pixel values. This is because in the subregion 71, the variations (amounts of change) between the pixel values are approximately a value $\alpha$ within the range of "$-\alpha$ to $\alpha$", and the frequency of the phase unwrapping error is low, and most of the pixel values are normal.

In the subdistributions $P_{1a}$, $P_{1b}$, $P_{2a}$, $P_{2b}$, $P_{3a}$ and $P_{3b}$, other than the subdistribution $P_0$, most of the pixel values are derived from the phase unwrapping error. The subdistributions $P_{1a}$, $P_{1b}$, $P_{2a}$, $P_{2b}$, $P_{3a}$, and $P_{3b}$ are approximately symmetrical about a peak of the subdistribution $P_0$. This is because the noise causing the phase unwrapping error is random and the phase unwrapping error has substantially equal probabilities for positive and negative values. Accordingly, the subdistributions $P_0$, $P_{1a}$, $P_{1b}$, $P_{2a}$, $P_{2b}$, $P_{3a}$ and $P_{3b}$ forms a binomial distribution as a whole.

The correction processing section 45 uses the mode $\psi_m$ as a reference value to correct the pixel values in each subregion 71. For example, the pixel value of the mode $\psi_m$ is used as a reference value (0). The pixel with a pixel value in the range of $-\alpha/2$ or more and less than $+\alpha/2$ is classified as the normal pixel having substantially no phase unwrapping error. The pixel with a pixel value in the range of $+\alpha/2$ or more and less than $+3\alpha/2$ is classified as an abnormal pixel with the $\alpha$ added to the pixel value due to the phase unwrapping error. A pixel with a pixel value in the range of $-3\alpha/2$ or more and less than $-\alpha/2$ is classified as an abnormal pixel with the $\alpha$ subtracted from the pixel value due to the phase unwrapping error. In a similar manner, the pixels in other ranges are also classified as the abnormal pixels.

The classification of pixels is described using a frequency histogram by way of example. The pixels are classified using an algorithm based on expressions. To be more specific, the correction processing section 45 calculates a difference $\Delta(x, y) = \psi(x, y) - \psi_m$ between each pixel value $\psi(x, y)$ and the mode $\psi_m$ in the subregion 71, and calculates an integer "n" which allows the difference $\Delta(x, y)$ to satisfy an expression (10). As shown by an expression (11), with the use of the integer n, the pixel value $\psi(x, y)$ is replaced with a pixel value $\psi'(x, y)$ calculated. The steps performed in the correction processing section 45 may be referred to as the correction processing.

$$n\alpha - \frac{\alpha}{2} \leq \Delta(x, y) < n\alpha + \frac{\alpha}{2} \quad (10)$$

$$\psi(x, y) \rightarrow \psi'(x, y) = \psi(x, y) - n\alpha \quad (11)$$

The phase unwrapping error is corrected in each subregion 71b by the correction processing of the pixel values based on the expressions (10) and (11). The "x, y" denotes coordinates of each pixel in the differential phase image 61. In the expression (10), a non-strict inequality sign ($\leq$) limits a lower limit of the difference $\Delta$, and a strict inequality sign ($<$) limits an upper limit of the difference $\Delta$. The strict and non-strict inequality signs are used as necessary as long as they specify a range in which the integer "n" is uniquely specified. For example, the expression (10) may be changed to an expression (10') $n\alpha - \alpha/2 < \Delta(x, y) \leq n\alpha + \alpha/2$.

The correction processing of the pixel values based on the expressions (10) and (11) is associated with the frequency histogram. The pixel values of the pixels in the subdistribution $P_0$ are not replaced because n=0. For each pixel in the subdistribution $P_{1a}$, "$\alpha$" is subtracted from the pixel value because n=1. For each pixel in the subdistribution $P_{1b}$, "$\alpha$" is added to the pixel value because n=−1. For each pixel in the subdistribution $P_{2a}$, "$2\alpha$" is subtracted from the pixel value because n=+2. For each pixel in the subdistribution $P_{2b}$, "$2\alpha$" is added to the pixel value because n=−2. In a similar manner, the product of the n and $\alpha$ (that is, "n·a") is added to or subtracted from the pixel value of each pixel in another subdistribution.

Figure 13:
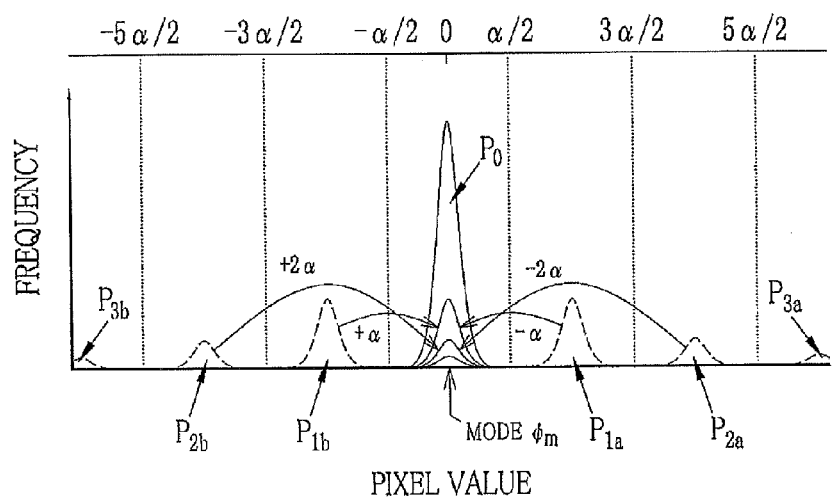
FIG. 13 is an explanatory view showing a relation between correction of the phase unwrapping error and the frequency histogram.

As described above, because most of the pixels in the subdistribution $P_0$ are the normal pixels with no phase unwrapping error, the correction of the pixel values is unnecessary. Most of the pixels in the subdistributions $P_{1a}$ and $P_{1b}$ are the abnormal pixels with the pixel values to each of which "$\alpha$" is added or subtracted due to the phase unwrapping error. To correct the phase unwrapping error, "$\alpha$" is added to or subtracted from each pixel value depending on the results of the expressions (10) and (11). Thus, the pixels with the corrected pixel values become the normal pixels. This means that the subdistributions $P_{1a}$ and $P_{1b}$ are moved such that their centers (modes) coincide with the mode $\psi_m$, as shown in FIG. 13. In a similar manner, the phase unwrapping error of the pixel value of each pixel in other subdistributions is corrected.

When the size of each subregion 71 is too large, for example, when each of the subdistributions $P_0$, $P_{1a}$, $P_{1b}$, and so forth widens such that tails of the subdistributions are connected to each other, it becomes difficult to distinguish the subdistributions from each other. In this case, the normal pixel that is supposed to be within the subdistribution $P_0$ may be positioned in an area in which the subdistributions $P_0$ and $P_{1a}$ are overlapped. As a result, the correction processing section 45 may erroneously perform the correction processing of the pixel value of the normal pixel in the overlapped area with the use of the expressions (10) and (11). On the other hand, when the size of each subregion 71 is too small, each of the subdistributions $P_0$, $P_{1a}$, $P_{1b}$, and so forth narrows down and the number of data in each subdistribution decreases. As a result, calculation accuracy of the mode $\psi_m$ deteriorates. This reduces the accuracy in the correction processing of the pixel values performed by the correction processing section 45.

The offset processing section 46 performs offset correction to the differential phase image after the phase unwrapping error is corrected by the correction processing section 45 as described above. The offset correction is to subtract an offset image from the differential phase image after the correction of the phase unwrapping error. Thereby, the noise superposed as the background noise on the differential phase image is subtracted. A noise component, being an offset value to be removed, is caused by, for example, distortion, slight displacement or misalignment (including rotation and tilting) of the first and second gratings 21 and 22 and moiré fringes caused by the distortion and the like.

After the phase unwrapping error is corrected and the offset is removed from the differential phase image, the phase contrast image producing section 47 integrates the differential phase image in the X direction to produce the phase contrast image representing the phase shift distribution. The offset-corrected differential phase image and the phase contrast image are stored in the image storage unit 16.

Figure 14:
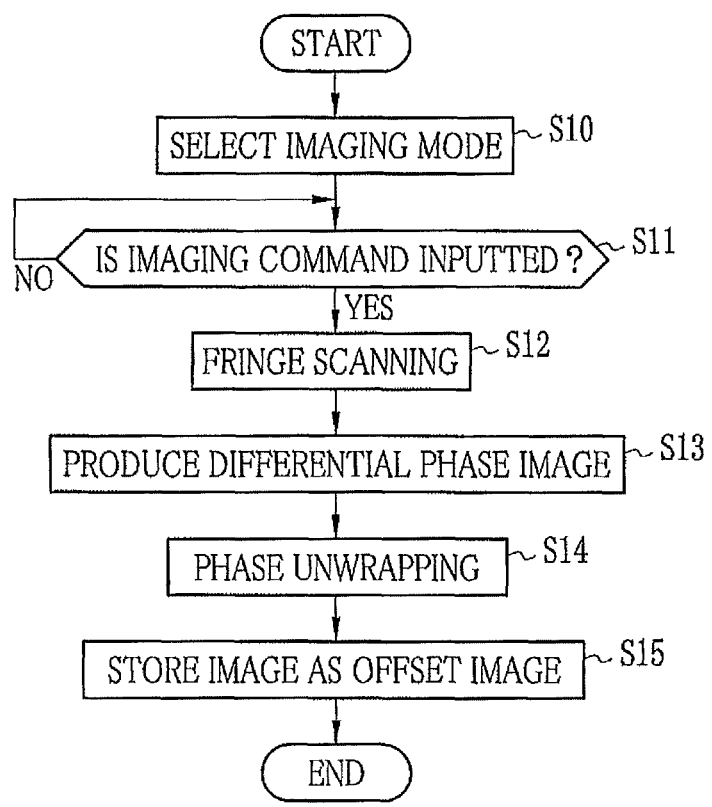
FIG. 14 is a flowchart showing steps of preliminary imaging.

Hereinafter, an operation of the X-ray imaging apparatus 10 is described. As shown in FIG. 14, the preliminary imaging is performed before the main imaging of the subject 9. When the preliminary imaging mode is selected using the operation unit 18a (S10), the X-ray imaging apparatus 10 is put on a standby until an imaging command is inputted (S11). When the imaging command is inputted using the operation unit 18a, the scan mechanism 23 translationally moves the second grating 22 at the predetermined scanning pitch to each of the scan positions k. The X-ray source 11 emits the X-rays and the X-ray image detector 13 detects the G2 image (S12) every time the second grating 22 is moved to one of the scan positions k. As a result of the fringe scanning, the M number of preliminary imaging data 51 are generated and stored in the memory 14.

The image processor 15 reads out the preliminary imaging data 51. In the image processor 15, the differential phase image producing section 40 produces the differential phase image from the preliminary imaging data 51 (S13). The differential phase image is unwrapped in the phase unwrapping section 41 (S14). Thereafter, the differential phase image is stored as an offset image in the offset image storage section 42. Thereby, the operation of the preliminary imaging is completed. Note that the preliminary imaging is carried out at least once in the absence of the subject 9, for example, when the X-ray imaging apparatus 10 is started. It is not necessary to carry out the preliminary imaging every time before the main imaging.

Figure 15:
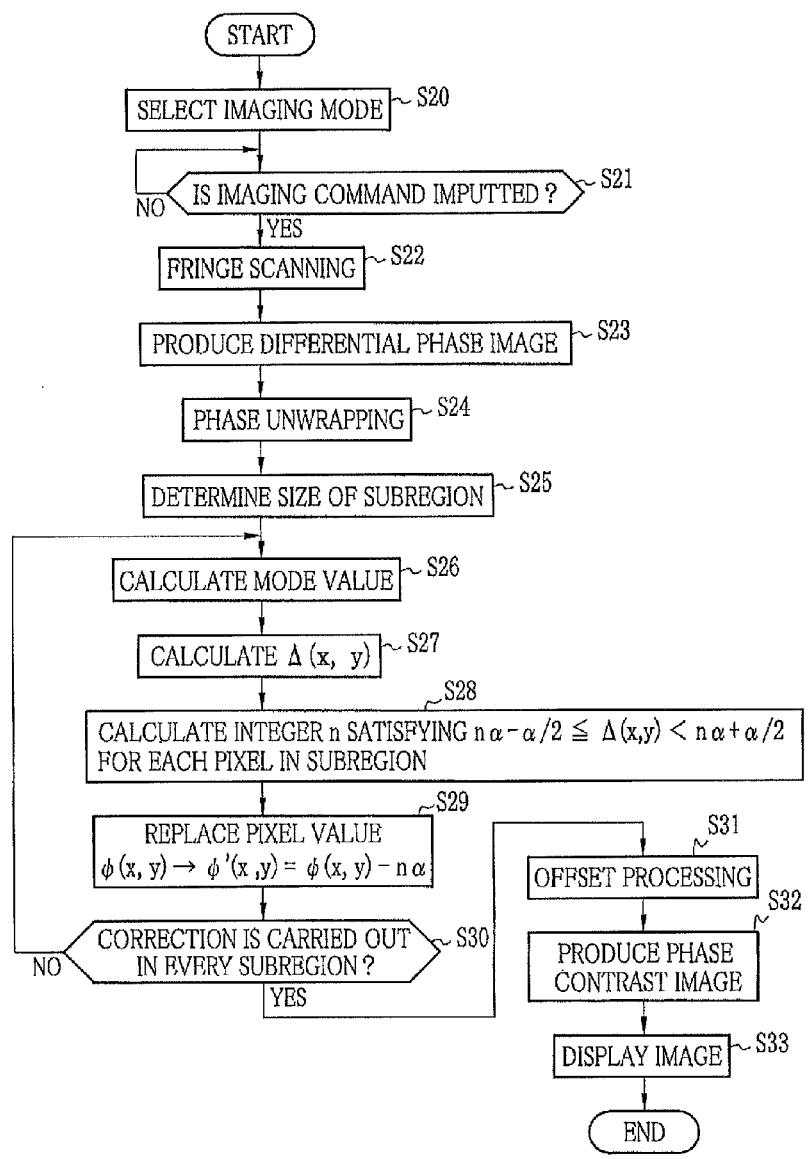
FIG. 15 is a flowchart showing steps of main imaging.

Next, the main imaging is carried out in the presence of the subject 9. To carry out the main imaging, as shown in FIG. 15, the main imaging mode is selected using the operation unit 18a (S20). When the main imaging mode is selected, the X-ray imaging apparatus 10 is put on the standby, ready to accept the imaging command (S21). When the imaging command is inputted using the operation unit 18a, the fringe scanning is performed (S22), and the M number of main imaging data 52 are stored in the memory 14.

Thereafter, the image processor 15 reads out the main imaging data 52. In the image processor 15, the differential phase image producing section 40 produces a first differential phase image K1 from the main imaging data 52 (S23). Then, the phase unwrapping section 41 carries out the phase unwrapping process of the first differential phase image K1 (S24). Thereafter, the first differential phase image K1 is inputted to the size determination section 43.

The size determination section 43 determines the optimum size of the subregion (S25). The subregion is a unit to be corrected. Namely, the subregion is a unit in which statistical operation and the correction processing are performed by the statistical operation section 44 and the correction processing section 45, respectively. Next, the statistical operation section 44 segments the differential phase image into the subregions with the size determined by the size determination section 43. The statistical operation section 44 calculates the mode $\psi_m$ of the pixel values in each of the subregions (S26). Then, the difference $\Delta(x, y)$ between the pixel value $\psi(x, y)$ of each pixel in the subregion and the mode $\psi_m$ is calculated (S27). Then, the integer "n" which allows the difference $\Delta(x, y)$ to satisfy the expression (10) is calculated (S28). Thereafter, the correction processing of the pixel value, corresponding to the integer "n", calculated based on the expression (11) is carried out (S29).

Of the above processing steps, the calculation of the mode (carried out by the statistical operation section 44) (S26), the calculation of the difference $\Delta(x, y)$ (carried out by the correction processing section 45) (S27), and the correction processing of the pixel value (S29) are performed for every subregion (S30). Thereby, the unwrapping error correction of the unwrapped differential phase image is completed.

When the processing steps (S26 to S29) carried out by the statistical operation section 44 and the correction processing section 45 are performed to every subregion and thus the unwrapping error correction is completed, the corrected differential phase image is inputted to the offset processing section 46. In the offset processing section 46, the differential phase image is subjected to the offset processing (S31) in which the offset image is subtracted from the differential phase image. The offset image is produced from the preliminary imaging and stored in advance. After the offset processing, the differential phase image is stored in the image storage unit 16.

At the same time, after the offset processing, the phase contrast image producing section 47 integrates the differential phase image to produce the phase contrast image (S32), and stores the phase contrast image in the image storage unit 16. Thereafter, the differential phase image which has been subjected to the offset processing and the phase contrast image are displayed on the monitor 18b (S33).

The X-ray imaging apparatus 10 corrects the phase unwrapping error as described above. Thus, the X-ray imaging apparatus 10 produces and displays the differential phase image and the phase contrast image both free from the phase unwrapping error.

To correct the phase unwrapping error, the X-ray imaging apparatus 10 segments the differential phase image into the subregions and calculates the mode $\psi_m$ in every subregion. This means that the phase unwrapping process itself is carried out along a predetermined path without distinguishing the bony part 66 and the like that are likely to cause the phase unwrapping error and without considering the presence and absence of the phase unwrapping error. With the use of the X-ray imaging apparatus 10, the differential phase image free from the phase unwrapping error is obtained easily when compared to the case where the phase unwrapping process is carried out while trying not to cause the phase unwrapping error, for example, the bony part 66 and the like are distinguished and avoided or a detour is made in the phase unwrapping process. Thus, the phase unwrapping error is corrected accurately regardless of the body part imaged.

The unwrapping error correction using the X-ray imaging apparatus 10 only needs the data of the differential phase image which has been subjected to the phase unwrapping process. Thus, the X-ray imaging apparatus 10 carries out the unwrapping error correction easily and accurately.

Figure 16:
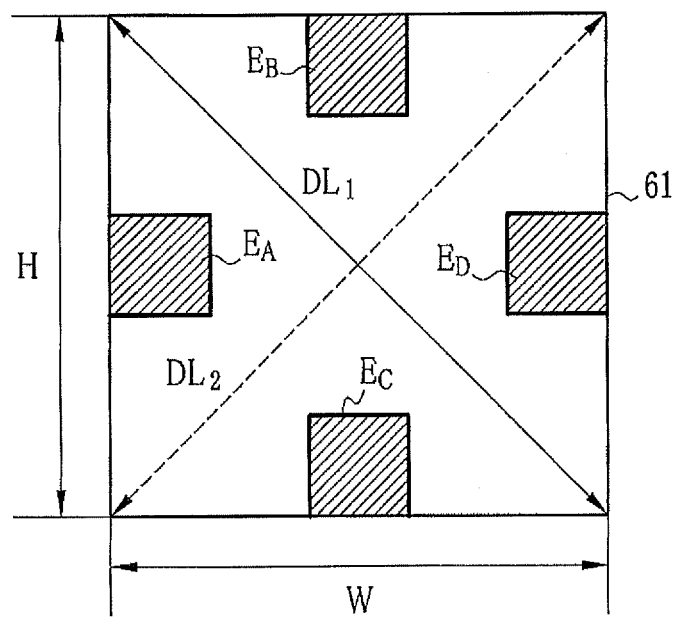
FIG. 16 is an explanatory view of another example showing how subregions are determined.

Note that, in the above embodiment, the average pixel values $\mu_A$, $\mu_B$, $\mu_C$, and $\mu_D$ of the predetermined regions $E_A$, $E_B$, $E_C$, and $E_D$ positioned in the corners of the differential phase image 61 are calculated, respectively, before the size of the subregions is determined by the size determination section 43, by way of example. The positions of the regions $E_A$, $E_B$, $E_C$, and $E_D$ are not limited to the above example and may be determined as necessary. For example, as shown in FIG. 16, the region $E_A$ may be positioned at the left side center of the differential phase image 61. The region $E_B$ may be positioned at the top center of the differential phase image 61. The region $E_C$ may be positioned at the bottom center of the differential phase image 61. The region $E_D$ may be positioned at the right side center of the differential phase image 61.

The maximum variation $N_W$ of the pixel values in the W direction is obtained from the expression $N_W=|\mu_A-\mu_D|$. The maximum variation $N_H$ in the H direction is obtained from the expression $N_H=|\mu_B-\mu_C|$. The maximum variation $N_{DL1}$ in the diagonal direction $DL_1$ is determined to be twice the value of the larger one of $|\mu_A-\mu_B|$ and $|\mu_D-\mu_C|$. Alternatively, the maximum variation $N_{DL1}$ may be determined to be twice the average of $|\mu_A-\mu_B|$ and $|\mu_D-\mu_C|$. The maximum variation $N_{DL2}$ in the diagonal direction $DL_2$ is determined in a similar manner. Even if the regions $E_A$, $E_B$, $E_C$, and $E_D$ are provided in positions different from those described above, the maximum variations $N_W$, $N_H$, $N_{DL1}$, and $N_{DL2}$ are calculated in a manner similar to the above embodiment or this modified example of the above embodiment. However, when the maximum variations $N_W$, $N_H$, $N_{DL1}$, and $N_{DL2}$ are calculated using the four regions $E_A$, $E_B$, $E_C$, and $E_D$, it is preferable to place the regions $E_A$, $E_B$, $E_C$, and $E_D$ in the respective corners of the differential phase image 61 as described in the above embodiment. This allows the longest distance between the regions, improving the calculation accuracy of the maximum variations $N_W$, $N_H$, $N_{DL1}$, and $N_{DL2}$.

In the above embodiment, the dimensions of each of the regions $E_A$, $E_B$, $E_C$, and $E_D$ are $0.1W \times 0.1H$ by way of example. The dimensions of the regions $E_A$, $E_B$, $E_C$, and $E_D$ are not limited to the above example and may be determined as necessary. However, when the regions $E_A$, $E_B$, $E_C$, and $E_D$ are too large or too small, the detection accuracy of the maximum variations $N_W$, $N_H$, $N_{DL1}$, and $N_{DL2}$ deteriorates. Accordingly, it is preferable that the dimensions of each of the regions $E_A$, $E_B$, $E_C$, and $E_D$ are in the order of $0.1W \times 0.1H$.

In the above embodiment, the four regions $E_A$, $E_B$, $E_C$, and $E_D$ are used to determine the size of the subregions, by way of example. The number of regions may be changed as necessary as long as the maximum variations $N_W$, $N_H$, $N_{DL1}$, and $N_{DL2}$ can be calculated. For example, a region $E_E$ (not shown) may be provided at the center of the differential phase image 61. The maximum variations $N_W$, $N_H$, $N_{DL1}$, and $N_{DL2}$ may be calculated taking account of an average $\mu_E$ of the pixel values of the pixels in the region $E_E$.

In the above embodiment, the differential phase image 61 is segmented into the subregions 71, and then each subregion 71 is subjected to the unwrapping error correction in an order indicated by an arrow shown in FIG. 11. The order of the unwrapping error correction may be changed as necessary. The unwrapping error correction of the adjacent subregions 71 is not necessarily carried out in sequence.

Figure 17:
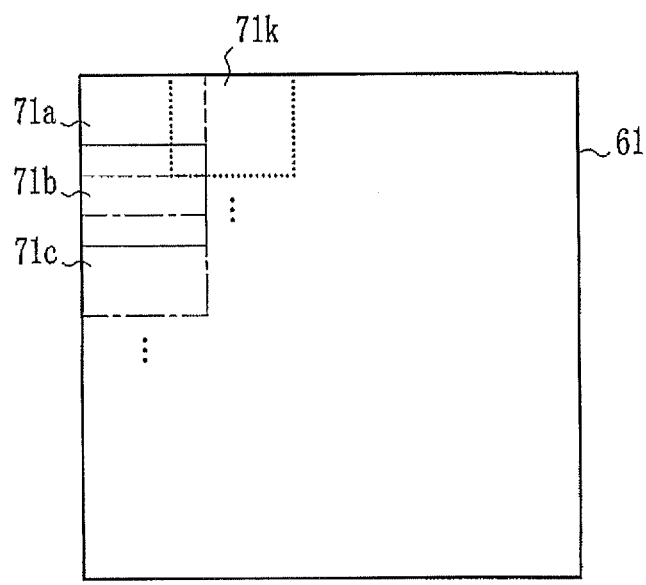
FIG. 17 is an explanatory view of another example showing how the phase unwrapping error is corrected.

In the above embodiment, the size of the subregions is determined such that the differential phase image 61 is segmented into rows and columns of the subregions without a remaining space. Alternatively, for example, as shown in FIG. 17, it is more preferable to determine the positions of subregions 71a, 71b, 71c, . . . , and 71k such that the adjacent subregions overlap each other to correct the phase unwrapping error throughout the differential phase image 61. To be more specific, the statistical operation section 44 determines the position of the subregion 71b such that an upper portion of the subregion 71b overlaps with a lower portion of the subregion 71a. The phase unwrapping error of the subregion 71b is corrected after the phase unwrapping error of the subregion 71a is corrected. Similarly, the statistical operation section 44 determines the position of the subregion 71c such that an upper portion of the subregion 71c overlaps with a lower portion of the subregion 71b. In the column of the subregions next to the leftmost column of the subregions in the differential phase image 61, the position of each subregion is determined such that a left portion of the subregion overlaps with right portion(s) of the subregion(s) in the leftmost column. For example, the left portion of the subregion 71k overlaps with the right portions of the subregions 71a and 71b. Thus, the positions of the subregions are determined to overlap each other. The phase unwrapping error of each subregion is corrected sequentially. Because the subregion includes the overlapped portion in which the phase unwrapping error has already been corrected, the peak value of the subdistribution $P_0$ is significantly higher than the peak values of the subdistributions $P_{1a}$, $P_{1b}$, and so forth even if the subregion contains a large amount of the phase unwrapping error. As a result, the mode $\psi_m$ is detected accurately, improving the accuracy of the unwrapping error correction. Note that, when there is no overlap between the subregions, the time for the unwrapping error correction in the differential phase image 61 is shorter than that of the subregions overlapped.

Note that the size of each subregion is determined by the size determination section 43 in a manner similar to the above embodiment even when the phase unwrapping error is corrected using the subregions overlapped each other. The variation (difference) between the pixel values in each subregion needs to be less than or equal to the range "α". Namely, the size of each subregion is at most the size calculated by the size determination section 43 or less. However, when the size of each subregion is too small, the accuracy of the correction processing performed by the correction processing section 45 deteriorates due to little data. It is preferable to make the size of the subregion similar to the size described in the above embodiment even if the subregions are positioned to overlap each other.

Note that, when the adjacent subregions are overlapped each other as described in the above embodiment, an amount of overlap may be determined as necessary. The detection accuracy of the mode $\psi_m$ improves as the amount of overlap increases. However, the time necessary for the unwrapping error correction increases as the amount of overlap increases. A specification or the like may set an upper limit to waiting time or loading time before the differential phase image or the phase contrast image is displayed on the monitor 18b. In this case, the time necessary for the unwrapping error correction and the subsequent processing is counted in advance, and the amount of overlap of the subregions and the size of each subregion may be adjusted to observe the time limit. Alternatively, the optimum amount of overlap may be determined in advance in view of the detection accuracy of the mode $\psi_m$ and the time necessary for the unwrapping error correction.

Note that, in the above embodiment, the size determination section 43 determines (changes) the optimum size of the subregions 71 in accordance with the offset superposed on the differential phase image, by way of example. Alternatively, the size of the subregions 71 may be fixed relative to the differential phase image. This is effective when the offset conditions are substantially fixed and do not vary in each imaging, because it allows omission of the calculation of the size of the subregions 71. As a result, the unwrapping error correction is completed in a shorter time. To fix the size of the subregions 71, the size of the subregions 71 may be determined in advance at the maintenance or calibration of the X-ray imaging apparatus 10 in a manner similar to the above embodiment. Note that, however, when the size of the subregions 71 is determined as described in the above embodiment, the phase unwrapping error is corrected accurately even if the offset conditions vary unexpectedly.

Note that, in the above embodiment, each subregion 71 is two-dimensional by way of example. Alternatively, each subregion 71 may be one-dimensional (a row or column of pixels, or a part of the row or column of the pixels).

Note that, in the above embodiment, the statistical operation (that is, the calculation of the mode $\psi_m$) in each subregion 71 and the correction processing of the pixel values are carried out sequentially on a subregion-by-subregion basis, by way of example. Alternatively, the statistical operation may be carried out in every subregions 71 first, and then the pixel values may be corrected in each subregion 71.

Note that, in the above embodiment, the statistical operation section 44 calculates the mode $\psi_m$ of the pixel values in each subregion 71, as a reference value used for the unwrapping error correction. The reference value may be other than the mode $\psi_m$. For example, an average or a median of the pixel values in each subregion 71 may be used as the reference value.

Figure 18:
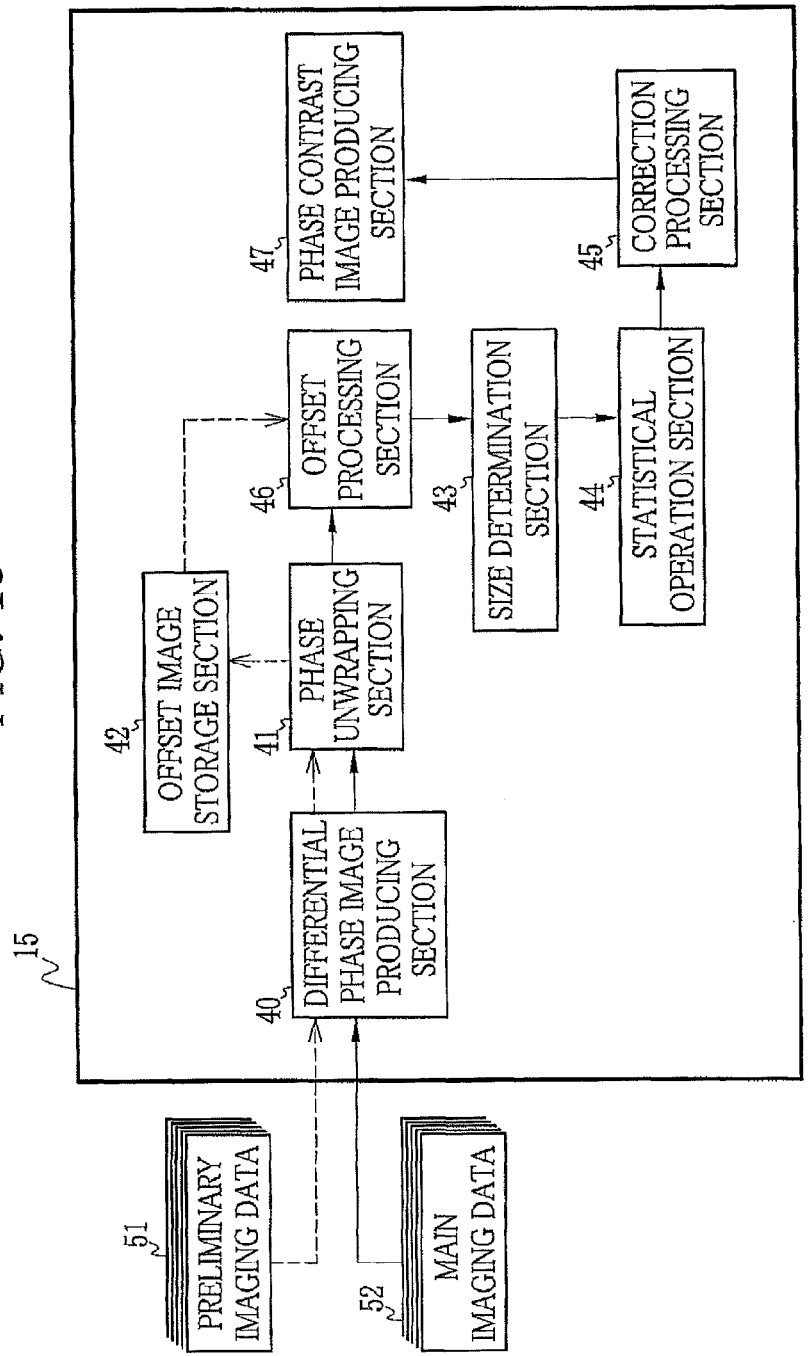
FIG. 18 is a block diagram of a configuration in which the phase unwrapping error is corrected after the offset processing.

Note that, in the above embodiment, the offset processing is carried out after the unwrapping error correction, by way of example. Alternatively, the phase unwrapping error may be corrected after the offset processing. For example, as shown in FIG. 18, the differential phase image unwrapped in the phase unwrapping section 41 is inputted to the offset processing section 46. After the offset processing in the offset processing section 46, the differential phase image is inputted to the size determination section 43 that determines the appropriate size of the subregions. Then, the statistical operation section 44 carries out the statistical operation. The correction processing section 45 carries out the correction processing of the phase unwrapping error. Thereafter, the differential phase image is inputted to the phase contrast image producing section 47.

Note that, in the above embodiment, the differential phase image and the phase contrast image are produced by way of example. Alternatively or in addition, an absorption image, a differential image of the absorption image, or a small angle scattering image may be produced from the preliminary imaging data 51 or the main imaging data 52. The absorption image is produced by imaging of average intensity of intensity modulation signals. The differential image of the absorption image is produced by differentiation of the absorption image in a predetermined direction (for example, the X direction). The small angle scattering image is produced by imaging of amplitudes of the intensity modulation signals.

When a defect occurs or dust is deposited on the X-ray image detector 13, the first grating 21, or the second grating 22, a pixel value of the pixel unit 30 may become extremely high or low. The region with the pixel defect has an abnormal average intensity, abnormal amplitude, and the like of the intensity modulation signals. Accordingly, the region with the pixel defect is likely to cause the phase unwrapping error. The present invention is also effective in correcting the phase unwrapping error caused by the pixel defect.

Because the phase unwrapping error caused by the pixel defect also occurs during the preliminary imaging, it is preferable to correct the phase unwrapping error during the preliminary imaging. The phase unwrapping error in the preliminary imaging is corrected in a manner similar to the unwrapping error correction in the main imaging described in the above embodiment.

Note that, in the above embodiment, the subject 9 is disposed between the X-ray source 11 and the first grating 21. Alternatively, the subject 9 may be disposed between the first grating 21 and the second grating 22.

In the above embodiment, the second grating 22 is moved in a direction (the X direction) orthogonal to a grating line (grid line) to carry out the fringe scanning. Alternatively, as described in Japanese Patent Application No. 2011-097090 filed by the assignee of the present invention, the second grating 22 may be moved in a direction (a direction not orthogonal to the X and Y directions in the XY plane) tilted relative to the grating line. In this case, the second grating 22 may be moved in any direction in the XY plane other than the Y direction. The scan positions "k" may be determined based on a component in the X direction of the movement of the second grating 22. Moving the second grating 22 in the direction tilted relative to the grating line increases a stroke (distance of the movement) necessary for the scanning of one period. This is advantageous in improving the accuracy of the movement.

In the above embodiment, the second grating 22 is moved to carry out the fringe scanning. Alternatively, the first grating 21 may be moved in a direction orthogonal to or tilted relative to the grating line.

In the above embodiment, the X-ray source 11 that emits the cone-shaped X-ray beams is used. Alternatively, an X-ray source which emits parallel X-ray beams may be used. In this case, the first and second gratings 21 and 22 are configured to substantially satisfy $p_2=p_1$ instead of the expression (1).

In the above embodiment, the X-rays from the X-ray source 11 are incident on the first grating 21. The X-ray source 11 has a single focal spot. The X-ray focal spot may be dispersed with a multi-slit (source grating) disposed immediately after the X-ray source 11 on the emission side as disclosed in U.S. Patent Application Publication No. 2009/0092227 (corresponding to WO2006/131235), for example. Thereby, the X-ray source with a high output is used. This increases the X-ray dose and improves the image quality of the differential phase image. It is necessary that a pitch $p_0$ of the multi-slit satisfies an expression (12). A distance $L_1$ denotes a distance between the multi-slit and the first grating 21.

$$p_0 = \frac{L_1}{L_2} p_2 \tag{12}$$

In the above embodiment, the first grating 21 projects the incident X-rays in a geometrical-optical manner. Alternatively, the first grating 21 may be configured to produce the Talbot effect as disclosed in U.S. Pat. No. 7,180,979 (corresponding to WO2004/058070), for example. To produce the Talbot effect with the first grating 21, an X-ray source with a small focal spot or the multi-slit may be used to improve spatial coherence of the X-rays.

When the Talbot effect is produced with the use of the first grating 21, the self image (G1) of the first grating 21 is formed downstream of the first grating 21 by the Talbot length $Z_m$ in the Z direction. This means that the distance between the first grating 21 and the second grating 22 needs to be set to the Talbot length $Z_m$.

The Talbot length $Z_m$ is determined by configuration of the first grating 21 and a shape of X-ray beams. When the first grating 21 is the absorption grating and the X-rays from the X-ray source 11 are cone-shaped beams, the Talbot length $Z_m$ is represented by an expression (13), where "m" denotes an integer.

$$Z_m = m \frac{p_1 p_2}{\lambda} \tag{13}$$

When the first grating 21 is a phase grating which provides phase modulation of $\pi/2$ to the X-rays and the X-rays from the X-ray source 11 are the cone-shaped beams, the Talbot length $Z_m$ is represented by an expression (14), where "m" is "0" or a positive integer.

$$Z_m = \left(m + \frac{1}{2}\right) \frac{p_1 p_2}{\lambda} \tag{14}$$

When the first grating 21 is a phase grating which provides phase modulation of $\pi$ to the X-rays and the X-rays from the X-ray source 11 are the cone-shaped beams, the Talbot length $Z_m$ is represented by an expression (15), where "m" is "0" or a positive integer.

$$Z_m = \left(m + \frac{1}{2}\right) \frac{p_1 p_2}{2\lambda} \tag{15}$$

When the first grating 21 is the absorption grating and the X-rays from the X-ray source 11 are parallel beams, the Talbot length $Z_m$ is represented by an expression (16), where "m" is a positive integer.

$$Z_m = m \frac{p_1^2}{\lambda} \tag{16}$$

When the first grating 21 is a phase grating which provides phase modulation of $\pi/2$ to the X-rays and the X-rays from the X-ray source 11 are the parallel beams, the Talbot length $Z_m$ is represented by an expression (17), where "m" is "0" or a positive integer.

$$Z_m = \left(m + \frac{1}{2}\right) \frac{p_1^2}{\lambda} \tag{17}$$

When the first grating 21 is a phase grating which provides phase modulation of $\pi$ to the X-rays and the X-rays from the X-ray source 11 are the parallel beams, the Talbot length $Z_m$ is represented by an expression (18), where "m" is "0" or a positive integer.

$$Z_m = \left(m + \frac{1}{2}\right)\frac{p_1^2}{4\lambda} \quad (18)$$

In the above embodiments, the grating unit 12 is provided with the first and second gratings 21 and 22. Alternatively, only the first grating 21 may be used, omitting the second grating 22.

For example, an X-ray image detector disclosed in Japanese Patent Laid-Open Publication No. 2009-133823 uses the first grating 21 only and allows omission of the second grating 22. The X-ray image detector is a direct conversion type provided with a conversion layer and charge collection electrodes. The conversion layer converts the X-rays into charge. Each charge collection electrode collects charge converted in the conversion layer. The charge collection electrode in each pixel is provided with a plurality of linear electrode groups. Each linear electrode group has linear electrodes arranged at a predetermined period and electrically connected to each other. The linear electrode groups are disposed out of phase each other. Each linear electrode group functions as the second grating 22. The linear electrode groups detect G2 images, out of phase each other, with the single image capture. Thus, this configuration omits the scan mechanism 23.

There is another method to produce the differential phase image based on single image data obtained with the X-ray image detector 13. In this method, the first and second gratings 21 and 22 are used, but the scan mechanism 23 is omitted. A pixel division method disclosed in Japanese Patent Application No. 2010-256241, filed by the assignee of the present invention, exemplifies the method. In the pixel division method, the first grating 21 and the second grating 22 are slightly rotated about the Z direction to cause moiré fringes in the G2 image. The moiré fringes have a periodicity in the Y direction. The single image data obtained with the X-ray image detector 13 is divided into groups each composed of a row of pixels (the pixels arranged in the X direction). The rows of pixels are out of phase each other relative to the moiré fringes. The divided pieces of the image data are regarded as those produced based on different G2 images formed by the fringe scanning. The differential phase image is produced in a manner similar to the above-described fringe scanning. In the pixel division method, the intensity modulation signal represents intensity changes in the pixel value in the single image data in a period of the moiré fringes.

A Fourier transform method disclosed in U.S. Patent Application Publication No. 2011/0158493 (corresponding to WO 2010/050483) is also known as a method to produce the differential phase image based on the single image data obtained with the X-ray image detector 13. The Fourier transform method uses the first and second gratings 21 and 22 but omits the scan mechanism 23 similar to the pixel division method. In the Fourier transform method, the single image data is subjected to the Fourier transform. Thereby, a Fourier spectrum is obtained. A spectrum (carrying the phase information) corresponding to a carrier frequency is separated from the Fourier spectrum, and inverse Fourier transform is performed. Thereby, a differential phase image is produced. Note that, in the Fourier transform method, the intensity modulation signal represents the intensity changes in the pixel value in the single image data in a period of the moiré fringes, similar to the pixel division method.

Note that, in the above embodiment, the phase unwrapping error caused by the phase unwrapping process in the differential phase image is corrected. The image processing method of the present invention is applicable to any image which has been subjected to the phase unwrapping process, regardless of whether the physical quantity of the pixel value is a differential phase value.

The present invention is applicable to radiation imaging apparatuses for industrial use and the like in addition to the radiation imaging apparatuses for medical diagnosing. Instead of the X-rays, the radiation may be gamma rays, for example.

Various changes and modifications are possible in the present invention and may be understood to be within the present invention.

What is claimed is:

1. An x-ray radiation imaging apparatus comprising:
   an x-ray radiation image detector for detecting x-ray radiation, emitted from an x-ray radiation source and passed through a subject, and producing image data;
   a grating unit disposed between the x-ray radiation source and the x-ray radiation image detector;
   a differential phase image producing section for producing a differential phase image based on the image data obtained with the x-ray radiation image detector, the differential phase image having pixel values wrapped into a range $-\alpha$ to $\alpha$;
   a phase unwrapping section for performing phase unwrapping process to the differential phase image;
   a statistical operation section for obtaining a reference value from statistical operation of pixel values of pixels in each subregion segmented in the differential phase image after the phase unwrapping process, each subregion being a unit in which error caused by the phase unwrapping process is to be corrected; and
   a correction processing section for correcting error caused by the phase unwrapping processing, the correction processing section calculating an integer n for each pixel with the pixel value different from the reference value in the respective subregion, the integer n allowing a difference $\Delta$ between a reference value and the pixel value to satisfy $n\alpha - \alpha/2 \leq \Delta < n\alpha + \alpha/2$, the correction processing section subtracting $n \cdot \alpha$ from the each pixel value.

2. The x-ray radiation imaging apparatus of claim 1, wherein the reference value comprises a mode of the pixel values in the respective subregion.

3. The x-ray radiation imaging apparatus of claim 1, further including a size determination section for determining size of the subregions based on the differential phase image after the phase unwrapping process.

4. The x-ray radiation imaging apparatus of claim 3, wherein the size determination section calculates a maximum variation between the pixel values in the differential phase image based on an average pixel value in each of predetermined regions in the differential phase image, and the size determination section determines the size of the subregions based on a ratio between the maximum variation and size of the differential phase image.

5. The x-ray radiation imaging apparatus of claim 4, wherein the regions are positioned in four respective corners of the differential phase image.

6. The x-ray radiation imaging apparatus of claim 3, wherein the size determination section determines the size of the subregions in accordance with a ratio of the size of the differential phase image such that a variation between the pixel values in the subregions is less than or equal to a value $\alpha$ within the range $-\alpha$ to $\alpha$.

7. The x-ray radiation imaging apparatus of claim 4, wherein the size determination section calculates the maximum variation between the pixel values in each of a width direction, a length direction, and a diagonal direction of the differential phase image based on the average pixel value, and the size determination section determines a width of the subregions based on the maximum variation in the width direction and the maximum variation in the diagonal direction, and the size determination section determines a length of the subregions based on the maximum variation in the length direction and the maximum variation in the diagonal direction.

8. The x-ray radiation imaging apparatus of claim 1, wherein the subregions are positioned to segment the whole differential phase image.

9. The x-ray radiation imaging apparatus of claim 1, wherein the adjacent subregions are positioned to overlap each other.

10. The x-ray radiation imaging apparatus of claim 1, further including:
  a storage section for storing the differential phase image, captured in absence of the subject, as an offset image; and
  an offset processing section for subtracting the offset image from the differential phase image with the phase unwrapping error corrected.

11. The x-ray radiation imaging apparatus of claim 1, wherein the grating unit is composed of a first grating and a second grating, and the first grating passes the x-ray radiation from the x-ray radiation source to form a first periodic pattern image, and the second grating partly blocks the first periodic pattern image to form a second periodic pattern image, and the x-ray radiation image detector detects the second periodic pattern image to produce the image data.

12. The x-ray radiation imaging apparatus of claim 11, wherein the grating unit is provided with a scan mechanism, and the scan mechanism moves the first grating or the second grating at a predetermined scan pitch and puts the first grating or the second grating to each of scan positions sequentially, and the x-ray radiation image detector detects the second periodic pattern image and produces the image data every time the first grating or the second grating is moved to one of the scan positions, and the differential phase image producing section produces the differential phase image based on the image data produced by the x-ray radiation image detector.

13. The x-ray radiation imaging apparatus of claim 12, wherein the scan mechanism moves the first grating or the second grating in a direction orthogonal to a grating line.

14. The x-ray radiation imaging apparatus of claim 12, wherein the scan mechanism moves the first grating or the second grating in a direction tilted relative to a grating line.

15. The x-ray radiation imaging apparatus of claim 11, wherein the differential phase image producing section produces the differential phase image based on the single image data obtained with the radiation image detector.

16. The x-ray radiation imaging apparatus of claim 11, wherein the first grating comprises an absorption grating that projects the incident radiation in a geometrical-optical manner to produce the first periodic pattern image.

17. The x-ray radiation imaging apparatus of claim 11, wherein the first grating comprises an absorption grating or a phase grating, and the first grating produces Talbot effect to produce the first periodic pattern image.

18. The x-ray radiation imaging apparatus of claim 11, further including a multi-slit for partly blocking the x-ray radiation from the radiation source to disperse a focal spot.

19. An image processing method comprising:
  (A) performing a phase unwrapping process to a differential phase image having pixel values wrapped into a range of $-\alpha$ to $\alpha$;
  (B) segmenting the differential phase image into subregions after the step (A), each of the subregions being a unit in which phase unwrapping error is to be corrected, each of the subregions containing pixels;
  (C) obtaining a reference value from statistical operation of the pixel values of the pixels in the respective subregion;
  (D) calculating an integer n for each pixel with the pixel value different from the reference value in the subregion, the integer n allowing a difference $\Delta$ between the reference value and the each pixel value to satisfy $n\alpha - \alpha/2 \leq \Delta < n\alpha + \alpha/2$;
  (E) subtracting $n \cdot \alpha$ from the each pixel value different from the reference value in the subregion to correct the phase unwrapping error; and
  (F) repeating steps (C), (D), and (E) until the phase unwrapping error is corrected in every subregion.

20. The image processing method of claim 19, further including:
  (G) determining size of each subregion based on the differential phase image after the step (A) and before the step (B).

* * * * *